(12) United States Patent
Maragni et al.

(10) Patent No.: US 10,377,732 B2
(45) Date of Patent: Aug. 13, 2019

(54) PROCESS FOR PREPARING AMINOTETRAHYDROPYRANS

(71) Applicant: F.I.S.—Fabbrica Italiana Sintetici S.p.A., Montecchio Maggiore (IT)

(72) Inventors: Paolo Maragni, Virgilio (IT); Massimo Verzini, Via Terme (IT)

(73) Assignee: F.I.S.—Fabbrica Italiana Sintetici S.p.A. (IT)

( * ) Notice: Subject to any disclaimer, the term of this patent is extended or adjusted under 35 U.S.C. 154(b) by 0 days.

(21) Appl. No.: 15/570,781

(22) PCT Filed: Nov. 29, 2016

(86) PCT No.: PCT/EP2016/079065
§ 371 (c)(1),
(2) Date: Oct. 31, 2017

(87) PCT Pub. No.: WO2017/093209
PCT Pub. Date: Jun. 8, 2017

(65) Prior Publication Data
US 2018/0290995 A1 Oct. 11, 2018

(30) Foreign Application Priority Data
Dec. 3, 2015 (EP) .................... 15197856

(51) Int. Cl.
| | | |
|---|---|---|
| *C07D 309/14* | (2006.01) | |
| *C07D 317/28* | (2006.01) | |
| *C07D 317/72* | (2006.01) | |
| *C07D 303/36* | (2006.01) | |
| *C07C 271/16* | (2006.01) | |
| *C07C 309/73* | (2006.01) | |
| *C07C 233/18* | (2006.01) | |

(52) U.S. Cl.
CPC .......... *C07D 309/14* (2013.01); *C07C 233/18* (2013.01); *C07C 271/16* (2013.01); *C07C 309/73* (2013.01); *C07D 303/36* (2013.01); *C07D 317/28* (2013.01); *C07D 317/72* (2013.01)

(58) Field of Classification Search
CPC ... C07D 309/14; C07D 317/28; C07D 317/72
See application file for complete search history.

(56) References Cited

U.S. PATENT DOCUMENTS

| | | | |
|---|---|---|---|
| 7,902,376 B2 | 3/2011 | Xu et al. | |
| 2009/0187028 A1* | 7/2009 | Xu ........................ | C07C 269/06 |
| | | | 548/218 |

FOREIGN PATENT DOCUMENTS

| | | |
|---|---|---|
| EP | 2358717 B1 | 8/2013 |
| WO | WO-2007126745 A2 | 11/2007 |
| WO | WO-2010056708 A1 | 5/2010 |
| WO | WO-2013003249 A1 | 1/2013 |
| WO | WO-2015139859 A1 | 9/2015 |

OTHER PUBLICATIONS

You. Advanced Synthesis and Catalysis, 2017, 359, 4260-66. (Year: 2017).*
Biftu, T., et al., "Omarigliptin (MK-3102): a Novel Long-Acting DPP-4 Inhibitor for Once-Weekly Treatment of Type 2 Diabetes," Journal of Medicinal Chemistry 57(8):3205-3212, American Chemical Society, United States (2014).
Blay, G., et al., "New Highly Asymmetric Henry Reaction Catalyzed by $Cu^{II}$ and a $C_1$-Symmetric Aminopyridine Ligand, and Its Application to the Synthesis of Miconazole," Chemistry a European Journal 14(15):4725-4730, Wiley-VCH, Germany (2008).
Chung, J.Y.L et al., "Evolution of a Manufacturing Route to Omarigliptin, a Long-Acting DPP-4 Inhibitor for the Treatment of Type 2 Diabetes," Organic Process Research & Development 19(11):1760-1768, American Chemical Society, United States (2015).
Eyer, M. and Seebach, D., "I-2-Nitro-1,3-alkanediols by Stereoselective Addition Nitroethanol to Aldehydes. On the Asymmetric Electrophilic Addition to Double Bonds," Journal of the American Chemical Society 107(12):3601-3606, American Chemical Society, United States (1985).
Gayet, A., et al., "Development of new camphor based N,S chiral ligands and their application in transfer hydrogenation," Organic & Biomolecular Chemistry 2(13):1887-1893, The Royal Society of Chemistry, England (2004).
International Search Report and Written Opinion for International Application No. PCT/EP2016/079065, European Patent Office, Rijswijk, Netherlands, dated Jan. 17, 2017, 11 pages.
Luzzio, F.A ., "The Henry reaction: recent examples," Tetrahedron 57:915-945, Elsevier Science Ltd., England (2001).
Xu, F., et al., "Asymmetric Synthesis of Highly Functionalized Tetrahydropyran DPP-4 Inhibitor," Organic Letters 16(20):5422-5425, American Chemical Society, United States (2014).
Yao, L., et al., "Promotion of Henry Reactions using $Cu(OTf)_2$ and a Sterically Hindered Schiff Base: Access to Enantioenriched β-Hydroxynitroalkanes " Tetrahedron 68(44):9119-9124, Elsevier Ltd., England (2012).

* cited by examiner

*Primary Examiner* — Noble E Jarrell
(74) *Attorney, Agent, or Firm* — Sterne, Kessler, Goldstein and Fox P.L.L.C.

(57) ABSTRACT

The present invention relates to a process for preparing 3-amino tetrahydropyrans and, more particularly, to an improved method for synthesizing a 2,3,5-substituted tetrahydropyran derivative, intermediate being used in the preparation of dipeptidyl peptidase-IV enzyme inhibitors (DPP-4 inhibitors).

18 Claims, No Drawings

PROCESS FOR PREPARING AMINOTETRAHYDROPYRANS

This Application is a national stage entry of the International Application No. PCT/EP2016/079065, filed Nov. 29, 2016, which claims the benefit of European Application No. EP15197856.6, filed on Dec. 3, 2015.

The present invention relates to a process for preparing 3-amino tetrahydropyrans and, more particularly, to an improved method for synthesizing a 2,3,5-substituted tetrahydropyran derivative, intermediate being used in the preparation of dipeptidyl peptidase-IV enzyme inhibitors (DPP-4 inhibitors).

3-amino tetrahydropyrans having 2R,3S,5R configuration of general formula

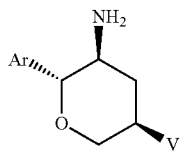

are known as excellent inhibitors of the dipeptidyl peptidase-IV enzyme (DPP-4 inhibitors) and are useful in the treatment or prevention of diseases in which said enzyme is involved such as diabetes and, especially, Type-2 diabetes.

Omarigliptin described chemically as (2R,3S,5R)-2-(2,5-difluoro-phenyl)-5-[2-(methyl-sulfonyl)-2,6-dihydro-pyrrolo[3,4-c]pyrazole-5(4H)-yl]-tetrahydro-2H-pyran-3-amine of formula

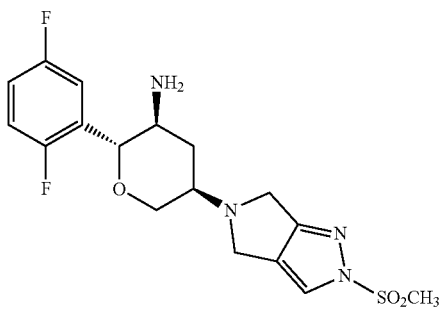 [SMILES: CS(=O)(=O)n1cc2c(n1)CN([C@H]1CO[C@H](c3cc(F)ccc3F)[C@@H](N)C1)C2]

is a 2,3,5-substituted tetrahydropyran analogue DPP-4 inhibitor indicated in the treatment of type 2 diabetes mellitus (T2DM).

The literature discloses various processes for preparing omarigliptin and/or DPP-4 inhibitor analogues thereof.

Patent EP 2358717 (Merck Sharp & Dohme Corp.) describes novel substituted aminotetrahydropyrans which are inhibitors of dipeptidyl peptidase-IV enzyme.

The preparation of said substituted aminotetrahydropyrans comprises the reaction of a compound of formula II with an amine of formula III

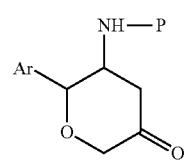

wherein Ar and V are defined in the document and P is a suitable nitrogen protecting group such as BOC and Cbz; under standard reductive amidation conditions followed by deprotection.

Particularly, the preparation of compound IIa is illustrated in Scheme 1 as well as in the experimental section:

SCHEME 1

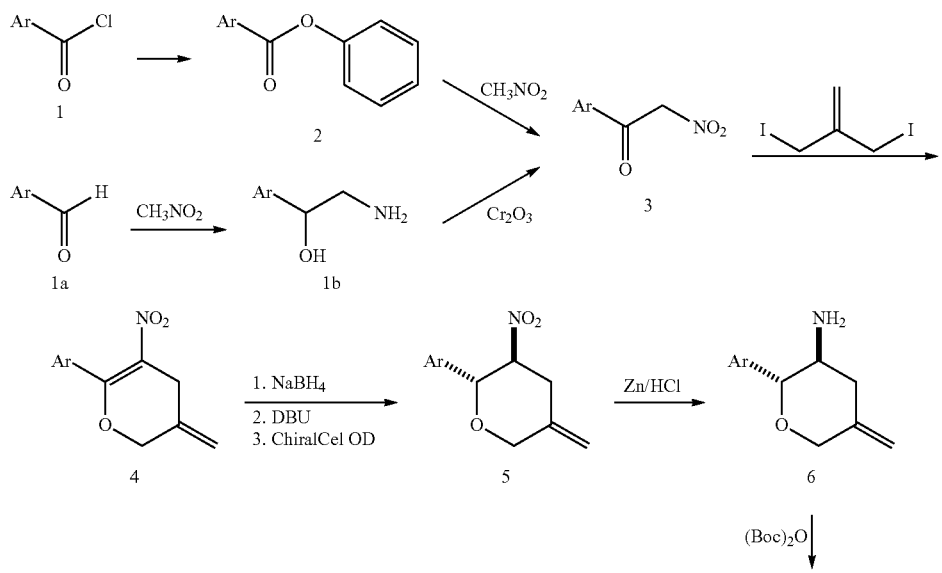

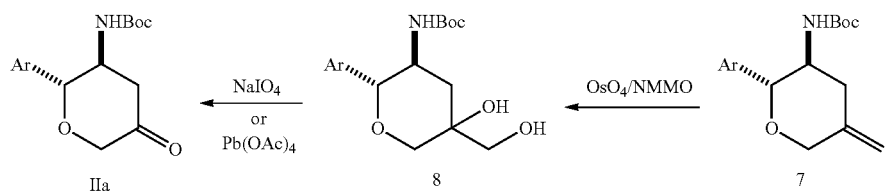
J. Med. Chem. 57 (2014), 3205-3212 describes a convergent synthesis of omarigliptin by reductive amination of tetrahydropyranone 8b with methylsulfonylpyrrolopyrazole 10 in the presence of triacetoxyborohydride in dimethylacetal to give intermediate 11 which is deprotected to the end-product; tetrahydropyranone 8a and 8b were prepared in accordance with Scheme 2 below:
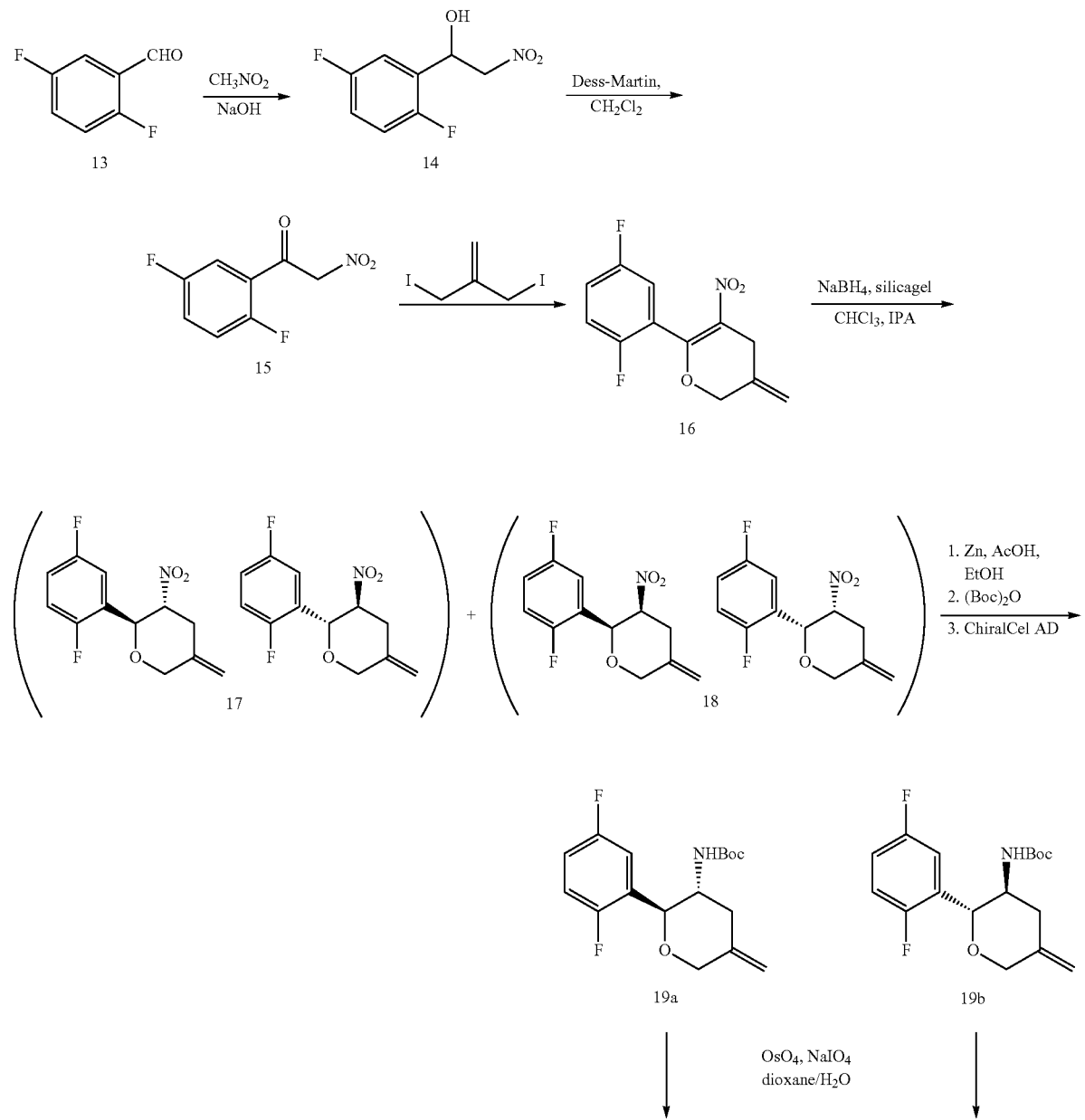

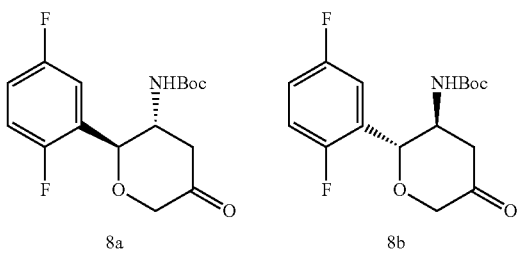

U.S. Pat. No. 7,902,376 patent (Merck Sharp & Dohme Corp.) describes a process for the preparation of chiral trans-2,3-disubstituted 5-oxotetrahydropyrans of formula

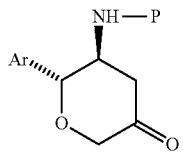

wherein Ar is optionally substituted phenyl and P is a primary amine protecting group; intermediates useful in the synthesis of dipeptidyl peptidase-IV inhibitors. International patent application WO 2013/003249 (Merck Sharp & Dohme Corp.) describes novel crystalline forms of a dipeptidyl peptidase-IV inhibitors; intermediate 1 of formula

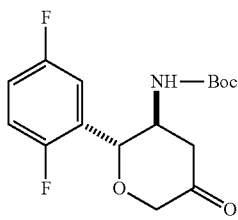 [SMILES: CC(C)(C)OC(=O)N[C@H]1CC(=O)CO[C@@H]1c1cc(F)ccc1F]

is prepared by a multi (a-o) steps synthesis where desired configuration is reached by, inter alia, three different back to back Ru-catalyzed reactions.

Organic Letters 16 (2014), 5422-5425 better describes the asymmetric synthesis of omarigliptin via Ru-catalyzed reactions; a Ru-catalyzed dynamic kinetic resolution reduction establishes two contiguous stereogenic centers first, a unique dihydropyran ring is constructed by a Ru-catalyzed cycloisomerization and hydroboration followed by a Ru-catalyzed oxidation affords the desired functionalized pyranone core scaffold.

Org. Process Res. Dev. 19 (2015), 1760-1768 describes the development of a convergent synthesis of Omarigliptin (MK-3102) that is amenable to multikilogram scale production. The synthesis of the desired pyranone relies on three Ru-catalyzed reactions both to control stereochemistry and enable bond constructions as described in the previous paper on Organic Letters (2014) above.

International patent application WO 2015/139859 (Fabbrica Italiana Sintetici S.p.A) describes an improved process for the preparation of key intermediates for the synthesis of the active ingredient named omarigliptin.

It is known in the art that the synthesis of chiral trans-2,3-disubstituted 5-oxotetrahydropyrans intermediates in the synthesis of DPP-4 inhibitors is challenging to a person skilled in the art on account of the asymmetric carbon atoms.

The synthetic approaches described in the art are identifiable as multi-step synthesis in which the overall yield and also the yields of the individual steps are highly penalizing from the industrial viewpoint.

In addition, producing the correct steric configuration of the chiral centers, in particular, contiguous R,S (C2, C3) stereochemical array with an S (C5) functionalized hydroxy group in the tetrahydropyran ring, respectively, proves to be a critical step of the synthetic process; in fact, the key issue of the art methods was the arduous nature of establishing the desired relative C2,C3 stereochemistry.

Therefore, being known in the art the essential role of functionalized tetrahydropyrans as key intermediates in the synthesis of DPP-4 inhibitors, it would be desirable to study improved methods which allow said intermediate to be prepared in good yields and under conditions that are more favorable from the point of view of the industrial application of the process. We have now surprisingly found an improved process for the synthesis of tetrahydropyran derivatives, key intermediates in the preparation of substituted aminotetrahydropyrans DPP-4 inhibitors, inter alia, omarigliptin by a catalytic nitro aldol reaction which makes it possible to overcome the drawbacks presented by the processes described in the prior art.

Therefore, it is an object of the present invention a process for preparing a compound of formula

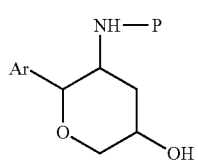

wherein Ar is phenyl optionally substituted with one to five R substituent/s each R independently selected from halogen, (C1-C4)-alkyl optionally substituted by halogen, (C1-C4)-alkoxy optionally substituted by halogen; and P is a primary amine protecting group; which comprises a. reacting a compound of formula

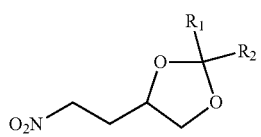

wherein each $R_1$ and $R_2$ is independently hydrogen and (C1-C4)-alkyl or taken together a (C3-C7)-cycloalkyl group; with a compound of formula Ar—CHO (III)

wherein Ar is defined above; in the presence of a basic species or a catalyst to give a compound of formula

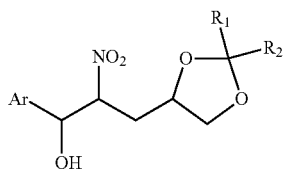

(IV)

wherein Ar, R1 and R2 are defined above;

b) converting a compound of formula IV into a compound of formula I. In one embodiment of the invention each of R is independently selected from fluorine, chlorine, methyl, trifluoromethyl and trifluoromethoxy; preferably, Ar is 2,5-difluorophenyl or 2,4,5-trifluorophenyl.

In a preferred embodiment of the invention Ar is 2,5-difluorophenyl.

In one embodiment of the invention each of R1 and R2 is independently selected from methyl and cyclohexyl when taken together.

In a preferred embodiment of the invention R1 and R2 is cyclohexyl when taken together.

The protection of the amine group takes place according to known techniques; P is a primary amine protecting group such as t-butyloxycarbonyl (Boc), benzyloxycarbonyl (Cbz), acetyl, 9-fluorenylmethyl-oxycarbonyl (FMOC), formyl, phthaloyl, benzoyl and pivaloyl.

In a preferred embodiment of the invention; P is selected from Boc, Cbz and acetyl group the acetyl group being the elected choice.

In the present invention, the term "halogen" means a fluorine, chlorine, bromine or iodine atom.

The compounds of formulae II and III may be prepared according to common synthetic techniques from commercially available substrates.

Literature describes some possible synthetic approaches to give a compound of formula II both in racemic and in optically active form.

It is evident to the skilled person that the use of a chiral compound of formula II allows fixing the steric configuration of the C5 of the tetrahydropyran ring and, in turn, of the active pharmaceutical isomers.

So, a compound of formula II in which R1 and $R_2$ are defined above, may be prepared according to the procedure which involves three steps according to the scheme reported hereinbelow:

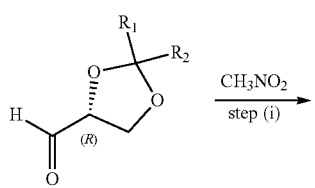

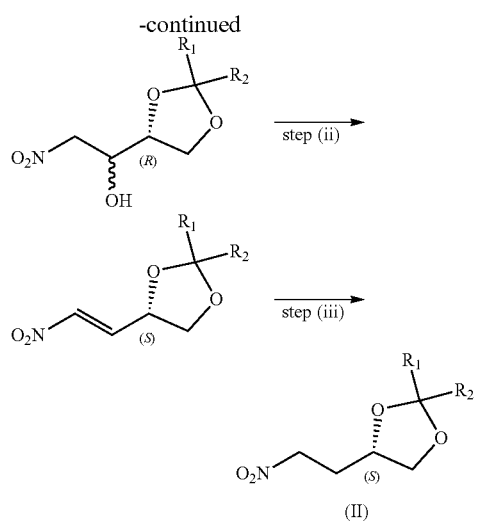

Step (i): nitro aldol reaction between the aldehyde substrate and nitromethane in the presence of a base, for example a source of fluoride ions, to give a nitro aldol adduct;

Step (ii): elimination (dehydration) to give a nitro-alkene;

Step (iii): reduction of the conjugated double bond to give the nitro-alkane of formula II.

Thus, in one embodiment of the invention, step (i) the aldehyde is reacted with nitromethane in EtOH. An aq. 10% solution of NaOH is added dropwise at 0° C. After about 0.5 hours, the reaction mixture is allowed to warm to room temperature and stirred overnight. The resulting mixture is quenched by addition of acetic acid and extracted with diethyl ether. The organic phases are washed with water, dried and concentrated to give the nitro-aldol as a crude product which is purified by flash chromatography on silica gel to give the pure product in a yield of about 75%. In step (ii), the nitro aldol is treated with triethylamine in DCM followed by methanesulfonyl chloride at 0° C. After a two hours at 20° C., the reaction mixture is quenched with aq. saturated solution of $Na_2CO_3$. The organic phase is separated and the aqueous phase is extracted two times with DCM. The combined organic phases are washed with saturated NaCl, dried and concentrated to give the dehydrated nitro-alkene product in a quantitative yield. In the final step (iii), the nitro-alkene is reduced by sequential treatment with N,N'-diphenylthiourea and Hantzsch ester in DCM at reflux. After 24 hours, the reaction mixture is cooled and concentrated under vacuum to give the crude product which is purified by flash chromatography on silica gel to give the nitro-alkane final product, of formula II in a yield around 80%.

In a preferred embodiment of the invention said nitroalkane of formula II is obtained as 3S isomer, namely (S)-2-(2-nitroethyl)-1,4-dioxaspiro[4.5]decane or (S)-2,2-dimethyl-4-(2-nitroethyl)-1,3-dioxolane.

The reaction of a compound of formula II with a compound of formula III to give a compound of formula IV is, generically, identifiable as a nitro-aldol or Henry reaction between a nucleophile generated from a suitable nitroalkane of formula II and an electrophile consisting of a suitable carbonyl compound III. The product of this reaction is a nitro aldol compound of formula IV.

The Henry reaction involves reacting the nitronate anion with a carbonyl group of aldehydes and ketones, forming a new C-C bond; nitro aldols (β-hydroxy nitro compounds) are thus obtained.

The reaction of a compound of formula II with a compound of formula III to give a compound of formula IV is, generally, performed in the presence of a basic species and/or an organometallic catalyst or, alternatively, a difunctional organic catalyst.

Generally, the reaction object of the invention is performed in organic solvents.

Solvents that are suitable for the coupling reaction of the compounds of formulae II and III are polar solvents such as alcohols like methanol and ethanol or apolar solvents such as hydrocarbons like toluene or polar aprotic solvents such as ethers, and, in particular diethoxyethane, 2,2-dimethoxypropane, 1,2-dimethoxyethane, THF and dioxane, the latter being preferred.

The reaction object of the invention is, generally, performed at a temperature comprised between −20° C. and 20° C. and, preferably, in a range between 0° C. and 20° C.

The reaction object of the invention is, generally, performed using a nitroalkane of formula II in a mole ratio comprised between 1 and 10 relative to the aldehyde substrate; preferably, the compound of formula II is used in excess relative to the substrate, more preferably in a mole ratio comprised between 4 and 6 and even more preferably 5.

The reaction is carried out in the presence of a suitable base to activate the nitroalkane. Suitable bases for the reaction object of the invention are ionic bases such as strong bases that are sources of hydroxyl ion (alkaline hydroxides, for instance NaOH), strong bases that are sources of alkoxide ions (alkaline alkoxides, for instance sodium methoxide), carbonates, for instance sodium carbonate and potassium carbonate or non-nucleophilic strong bases of the tertiary amine type such as triethylamine (TEA) and N,N-diisopropylethylamine (DIPEA).

Preferably, the base is used relative to the substrate in a mole ratio comprised between 0.1 and 1. More preferably the base is used in a mole ratio of 0.1.

In an alternative preferred aspect of the invention, the reaction of a compound of formula II with a compound of formula III to give a compound of formula I is performed in the presence of a catalyst.

The catalyst object of the invention is an organometallic catalyst, among which the preferred ones are organometallic complexes of Cu(II) or Cu(I) with chiral ligands (C2-symmetric or C1-symmetric) such as sterically hindered ligands derived from cinchona alkaloids and ligands derived from optically active diamines, for instance, the known derivatives of chiral 1,2-diaminocyclohexanes or other chiral diamines such as 1,2-diphenylethylenediamine, 2,2'-binaphthyldiamines and amino pyridine ligands.

Ligands of the invention are selected among:
2,4-di-tert-butyl-6-((E)-((R)-(6-methoxyquinolin-4-yl)((2R,4S,8R)-8-vinylquinuclidin-2-yl)methylimino)methyl)phenol or, alternatively, named as 2,4-bis(1,1-dimethylethyl)-6-[(E)-[[(9R)-6'-methoxycinchonan-9-yl]imino]methyl]-phenol (ligand G);
2,4-di-tert-butyl-6-(((R)-(6-methoxyquinolin-4-yl)((2R,4S,8R)-8-vinylquinuclidin-2-yl)methylamino)methyl)phenol;
6,6'-(1R,2R)-cyclohexane-1,2-diylbis(azanediyl)bis(methylene)bis(2,4-di-tert-butylphenol);
6,6'-(1E,1'E)-(1R,2R)-cyclohexane-1,2-diylbis(azan-1-yl-1-ylidene)bis(methan-1-yl-1-ylidene)bis(2-tert-butylphenol);
(1R,2R,N1E,N2E)-N1,N2-bis(pyridin-2-ylmethylene)cyclohexane-1,2-diamine;
(1R,2R)-N1,N2-bis(pyridin-2-ylmethyl)cyclohexane-1,2-diamine;
(1R,2R,N1E,N2E)-1,2-diphenyl-N1,N2-bis(pyridin-2-ylmethylene)ethane-1,2-diamine;
(1R,2R)-1,2-diphenyl-N1,N2-bis(pyridin-2-ylmethyl)ethane-1,2-diamine.

Preferably, ligands of the invention are selected among:
(1R,2R)-N1,N2-bis(4-pyridinylmethyl)-1,2-cyclohexanediamine (ligand A);
2-(1,1-dimethylethyl)-6-[[[(1R,2R)-2-[(4-pyridinylmethyl)amino]cyclohexyl]amino]methyl]-phenol (ligand B);
2,2'-[(1R,2R)-1,2-cyclohexanediylbis(iminomethylene)]bis[6-(1,1-dimethylethyl)-phenol] (ligand C);
2-(1,1-dimethylethyl)-6-[[[(1S,2S)-2-[(4-pyridinylmethyl)amino]cyclohexyl]amino]methyl]-phenol (ligand D); and
2,4-di-tert-butyl-6-((E)-((R)-(6-methoxyquinolin-4-yl)((2R,4S,8R)-8-vinylquinuclidin-2-yl)methylimino)methyl) phenol (ligand G).

More preferably the chiral ligand is a camphor derived C1-symmetric chiral aminopyridine ligand derived from D-(+)-camphor (natural) or L-(−)-camphor (non-natural) and 2-pyridinemethanamine (pycolilamine), N-[(1R,2R,4R)-1,7,7-trimethylbicyclo[2.2.1]hept-2-yl]-2-Pyridinemethanamine (Ligand E) and N-[(1S,2S,4S)-1,7,7-trimethylbicyclo[2.2.1]hept-2-yl]-2-Pyridinemethanamine (Ligand F), respectively.

Even more preferably the chiral ligand is a C1-symmetric chiral aminopyridine ligand derived from the non-natural L-(−)-camphor (also denoted as (1S,4S)-(−)-camphor) and 2-pyridinemethanamine obtained from a reductive amination reaction.

The two-step procedure for the synthesis of the desired chiral ligand F derived from non-natural camphor is the same as for the literature synthesis of its enantiomer, derived from natural camphor which is described in Org. Biomol. Chem. 2004, 2, 1887-1893 and Chem. Eur. J. 2008, 14, 4725-4730.

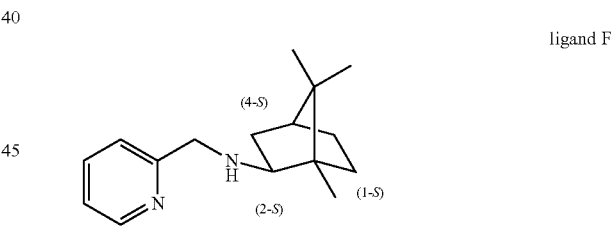

ligand F

So, according to a two-step procedure: (1S,4S)-(−)-camphor) is reacted with 2-pyridinemethanamine in the presence of BF3.Et2O in toluene at reflux to form the corresponding iminopyridine; then, the imine C=N double bond is reduced upon treatment of NaBH4/NiCl2 in methanol at −30° C. to give the (1S,2S,4S)-aminopyridine corresponding to ligand F as the major isomer. The minor amount of the (1S,2R,4S)-aminopyridine diastereoisomer is separated by chromatography.

Alternatively, in a preferred embodiment of the invention, the chiral ligand is a sterically hindered ligand derived from cinchona alkaloids such as 2,4-di-tert-butyl-6-((E)-((R)-(6-methoxyquinolin-4-yl)((2R,4S,8R)-8 -vinylquinuclidin-2-yl)methylimino)methyl)phenol (ligand G).

The procedure for the synthesis of the desired chiral ligand above is the same as for the literature synthesis of its enantiomer which is described in Tetrahedron (2012), 68, 9119-9124.

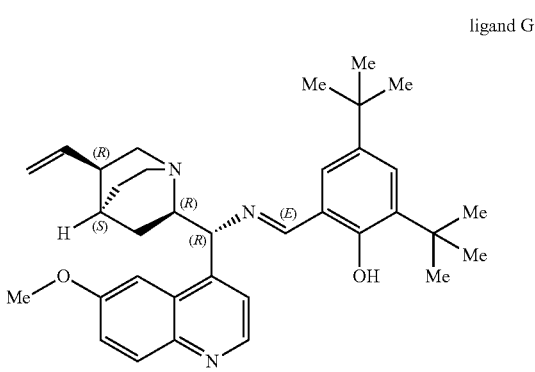

ligand G

So, according to a literature procedure: a solution of (8R,9R)-9-amino-(9-deoxy)-epiquinidine and 3,5-di-tert-butylsalicylaldehyde in absolute ethanol (20 mL) was heated to reflux.

After that, dried MgSO4 was added to the solution; after 5-8 h, the mixture was slowly cooled down to room temperature and filtrated. The solvent was evaporated under reduced pressure.

The crude product was purified by flash chromatography on silica gel to afford the Schiff base ligand G as a yellow solid.

The use of a catalyst in the nitro-aldol reaction object of the invention was shown to be surprisingly efficient in terms of conversion/yield and, mainly, of stereo selection since it is capable of directing said reaction toward a product of formula IV having the desired steric anti-configuration of the two newly created chiral centers (C1, C2), in particular, contiguous R,S (C1, C2) stereochemical array.

It is clear to a person skilled in the art that an enrichment of the diastereoisomeric mixture promotes simplification of the processes for separating the optical isomers that are useful in the preparation of the pharmaceutical active ingredients.

In one embodiment of the invention, the reaction of a compound of formula II with a compound of formula III to give a compound of formula IV is performed in the presence of an organometallic chiral complex of Cu(II) generated in situ by mixing for instance copper diacetate Cu(OAc)$_2$ or copper bis(trifluoromethanesulfonate) Cu(OTf)$_2$ with a chiral ligand such as sterically hindered ligands derived from cinchona alkaloids and ligands derived from optically active diamines, for instance a chiral 1,2-diaminocyclohexane derivative, or other chiral diamines such as 1,2-diphenylethylenediamine, 2,2'-binaphthyldiamines and preferably aminopyridine ligands.

More preferably the chiral ligand is a L-(−)-camphor-derived aminopyridine ligand: N-[(1S,2S,4S)-1,7,7-trimethylbicyclo[2.2.1]hept-2-yl]-2-Pyridinemethanamine (Ligand F).

Even more preferably the chiral ligand is 2,4-di-tert-butyl-6-((E)-((R)-(6-methoxyquinolin-4-yl)((2R,4S,8R)-8-vinylquinuclidin-2-yl)methylimino)methyl)phenol (ligand G).

Preferably, the catalyst is used relative to the substrate in an amount comprised between 1 and 10 mol %, more preferably in a 5 mol % amount.

In a preferred aspect of the invention, the catalyst is formed in situ by mixing the Cu(II) salt for instance Cu(OTf)$_2$ and the L-(−)-camphor-derived aminopyridine ligand (Ligand F) in dioxane at 0-4° C.

After addition of a suitable non-nucleophilic tertiary amine base for instance TEA, a solution of nitroalkane of formula II in dioxane, in a variable excess (e.g. 5 moleq.), is added followed by a dropwise addition of the 2,5-difluorobenzaldehyde. The resulting mixture is allowed to warm to room temperature and stirred for 48 hours.

The mixture is concentrated, diluted with EtOAc and washed with water. The resulting organic phase is dried and concentrated under vacuum to give the crude product that is purified by flash chromatography on short silica gel column to give the nitro aldol of general formula IV in a 55-75% yield as a mixture of diastereoisomers where the major product is the desired with anti-(1R,2S)-configuration at the two newly created chiral centers (C1, C2).

In an alternative preferred aspect of the invention, the catalyst is formed in situ by mixing the Cu(II) salt for instance Cu(OTf)$_2$ and the cinchona alkaloids derived ligand G in THF.

A solution of nitroalkane of formula II in THF, in a variable excess (e.g. 5 mol eq.), is added followed by a dropwise addition of the 2,5-difluorobenzaldehyde.

After addition of a suitable non-nucleophilic tertiary amine base for instance TEA at around −20° C., the resulting mixture is stirred for 24 hours.

The mixture is quenched, then, diluted with EtOAc and washed with water. The resulting organic phase is dried and concentrated under vacuum to give the crude product that is purified by flash chromatography on short silica gel column to give the nitro aldol of general formula IV in a 55-75% yield as a mixture of diastereoisomers where the major product is the desired with anti-(1R,2S)-configuration at the two newly created chiral centers (C1, C2). Therefore, it is a further object of the invention a process for preparing a compound of formula

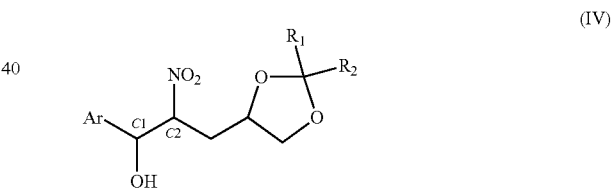

(IV)

wherein Ar, R1 and R2 are defined above; which comprises a. reacting a compound of formula

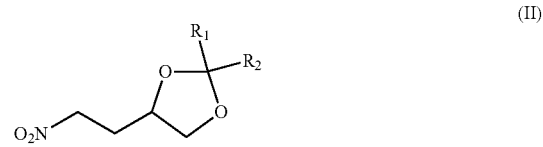

(II)

wherein R$_1$ and R2 are defined above; with a compound of formula

Ar—CHO (III)

wherein Ar is defined above; in the presence of a basic species or a catalyst.

The nitro aldol of formula IV is converted by chemoselective reduction of the nitro group into the corresponding amino-alcohol of formula V.

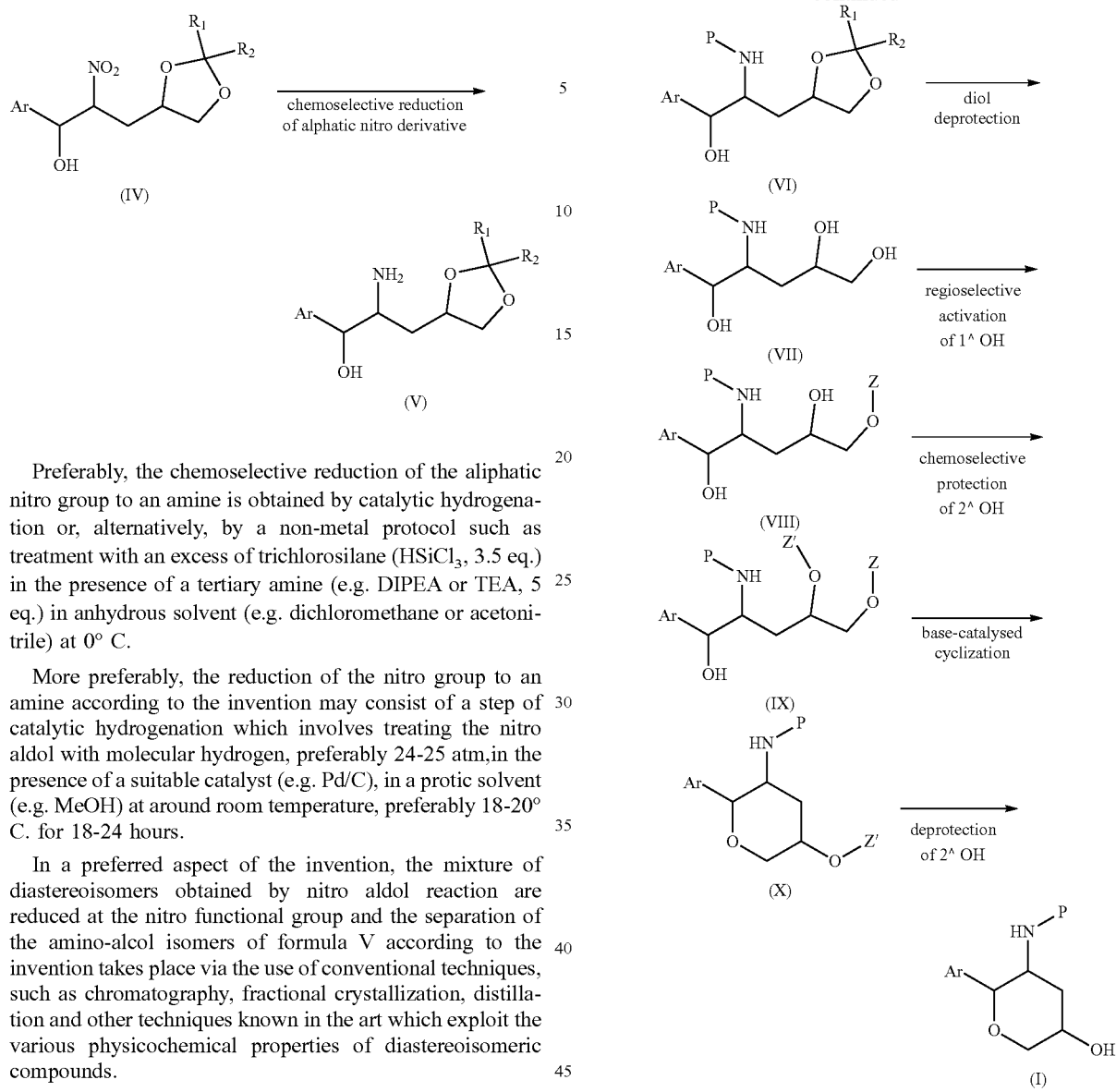

Preferably, the chemoselective reduction of the aliphatic nitro group to an amine is obtained by catalytic hydrogenation or, alternatively, by a non-metal protocol such as treatment with an excess of trichlorosilane (HSiCl₃, 3.5 eq.) in the presence of a tertiary amine (e.g. DIPEA or TEA, 5 eq.) in anhydrous solvent (e.g. dichloromethane or acetonitrile) at 0° C.

More preferably, the reduction of the nitro group to an amine according to the invention may consist of a step of catalytic hydrogenation which involves treating the nitro aldol with molecular hydrogen, preferably 24-25 atm, in the presence of a suitable catalyst (e.g. Pd/C), in a protic solvent (e.g. MeOH) at around room temperature, preferably 18-20° C. for 18-24 hours.

In a preferred aspect of the invention, the mixture of diastereoisomers obtained by nitro aldol reaction are reduced at the nitro functional group and the separation of the amino-alcol isomers of formula V according to the invention takes place via the use of conventional techniques, such as chromatography, fractional crystallization, distillation and other techniques known in the art which exploit the various physicochemical properties of diastereoisomeric compounds.

In one aspect of the invention, the compounds of general formula V are separated on a chromatographic column using silica gel (flash) as stationary phase and a DCM/methanol (95/5)+0.5% trifluoroacetic acid (TFA) mixture as mobile phase to give two out of the four possible diastereoisomers of the invention.

In one embodiment of the invention, one or more of the four products of general formula V are used separately in the following steps according to the scheme reported below

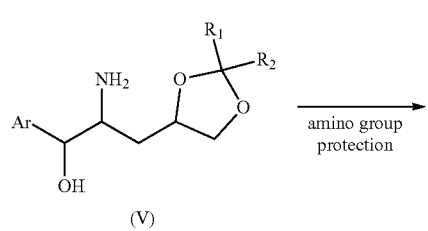

to give a compound of formula I wherein Ar and P are defined above.

In particular, the amine compound of formula V is, in turn, protected according to common synthetic techniques, wherein P is defined above, to give a compound of formula VI.

A compound VI as single diastereoisomer or a mixture of diastereoisomers is, then, deprotected from the acetonide to give diol compound VII which is, in turn, regioselectively functionalized at the distal 1^ hydroxy group so as to convert said hydroxy residue into a good leaving group and to give a compound VIII.

In a preferred embodiment of the invention, said distal 1^ hydroxy group is activated by reaction with an organo sulfonyl group such as an alkylsulfonyl or arylsulfonyl group.

More preferably, said distal 1^ hydroxy group is activated by reaction with an organo sulfonyl group selected among methanesulfonyl (mesyl), benzenesulfonyl (besyl), 4-nitrobenzene-1-sulfonyl (nosyl) and 4-methylbenzene-1-sulfonyl (tosyl); the latter being the preferred one.

Compound VIII is chemoselectively protected at the distal 2^ hydroxy group to give a compound IX, also exploiting the unexpected poor reactivity of the benzylic hydroxy group. Z' protecting group according to the invention are common hydroxy protecting group and are preferably selected from tetrahydropyranyl (THP), acetyl (Ac), trialkylsilyl (trimethylsilyl TMS, tert-butyldimethylsilyl TBDMS), tetrahydropyranyl (THP) group being preferred.

Finally, a compound of formula IX is converted into a compound of formula X according to the invention by a base-catalyzed cyclization step; compound X is, in turn, converted into a compound of formula I by an acid catalyzed deprotection step.

In one aspect of the invention, compound VIII is reacted with 3,4-dihydropyran and p-TsOH in DCM at room temperature and crude product IX obtained after solvent removal is re-dissolved in dry THF.

The solution of compound IX in THF is added dropwise to a slurry of NaH in THF at 0° C. The resulting mixture is stirred at room temperature, then quenched with aq. HCl and diluted with EtOAc. After further back-extraction of the aqueous phase the combined organic phases are dried and concentrated under vacuum to obtain a crude product containing the desired product of formula I in mixture with the compound of formula X still protected at the hydroxyl group as THP which is, in turn, converted into a compound of formula I by an acid catalyzed deprotection step.

Alternatively, the amine-alcol compound of formula V is, in turn, bis-protected according to common synthetic techniques, to give a compound of formula VIbis

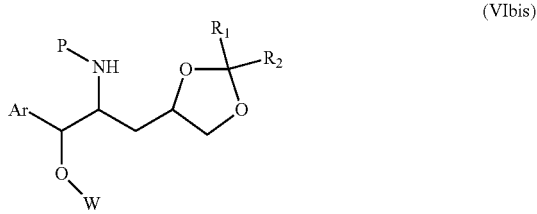

(VIbis)

wherein Ar, R1, R2 and P are defined above and W has the same meanings of Z'above. Said compound VIbis undergoes acetonide deprotection, regioselective functionalization at the distal 1^ hydroxy group and chemoselective protection at the distal 2^ hydroxy group to give correspondent compounds VIIbis, VIIIbis and IXbis where benzylic OH— residue is protected (—W), the latter being subsequently converted into a compound of formula X according to the invention.

Alternatively, a compound of formula VIII is converted into a compound of formula

(XI)

wherein Ar and P are defined above in the presence of a base; compound XI is, in turn, converted into a compound of formula I in accordance with conventional techniques.

In one aspect of the invention, compound VIII in THF is added dropwise to a slurry of NaH in THF at 0° C.

The resulting mixture is stirred at room temperature, then quenched with aq. ammonium chloride and diluted with EtOAc.

After further back-extraction of the aqueous phase the combined organic phases are dried and concentrated under vacuum to obtain a crude product containing the desired product of formula XI.

Oxirane compound XI is converted into a compound of formula I according to common epoxide 6-endo-type cyclization techniques, for instance, by following teachings disclosed in the International patent application WO 2015/139859 (Fabbrica Italiana Sintetici S.p.A.) step 1 page 19, paragraph [0070] above mentioned.

Therefore, it is a further object of the present invention a process for preparing a compound of formula

(I)

wherein Ar and P are defined above which comprises preparing a compound of formula IV as above described; and further comprising c. chemoselective reduction of aliphatic nitro derivative to give amino-alcohol of formula

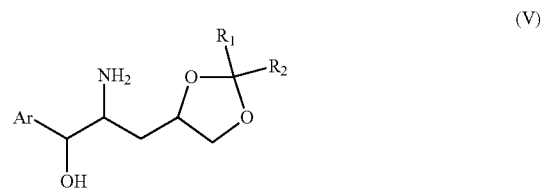

(V)

wherein Ar, R1 and R2 are defined above;

d. protection of amino group to give a compound of formula

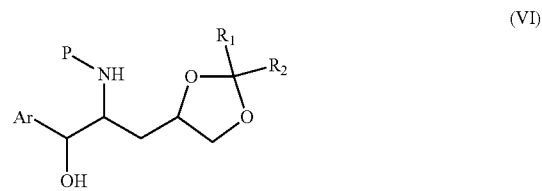

(VI)

w wherein P is defined above;

e. deprotection of diol residue to give a compound of formula

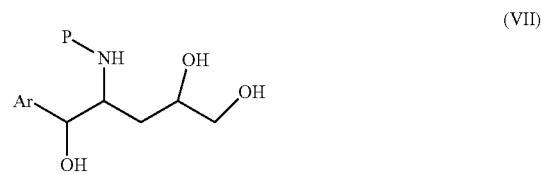

(VII)

f. regioselective activation of primary hydroxy group to give a compound of formula

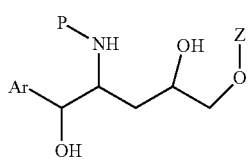
(VIII)

wherein Z is an organo sulfonyl group;

g. chemoselective protection of secondary hydroxy group to give a compound of formula

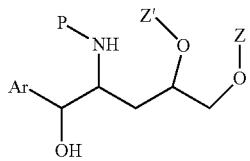
(IX)

wherein Z' is a hydroxy protecting group;

h. base-catalyzed cyclization to give a compound of formula

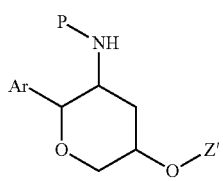
(X)

i. deprotection of secondary hydroxy group to give a compound of formula I.

Therefore, it is a further object of the present invention a process for preparing a compound of formula

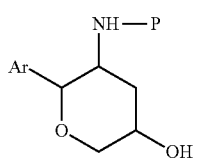
(I)

wherein Ar and P are defined above which comprises preparing a compound of formula IV as above described; and further comprising c. chemoselective reduction of aliphatic nitro derivative to give amino-alcohol of formula

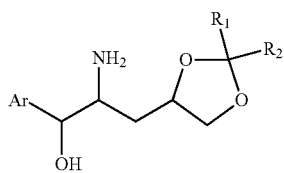
(V)

wherein Ar, R1 and R2 are defined above;

d. bis-protection of amino and hydroxy groups to give a compound of formula

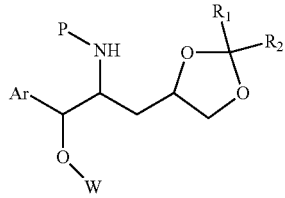
(VIbis)

wherein P is defined above and W is hydroxy protecting group;

e. deprotection of diol residue to give a compound of formula

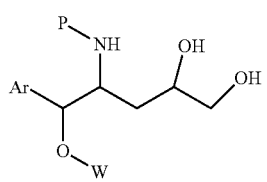
(VIIbis)

f. regioselective activation of primary hydroxy group to give a compound of formula

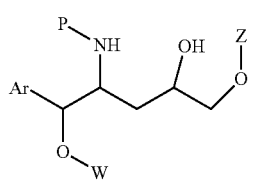
(VIIIbis)

wherein Z is an organo sulfonyl group;

g. chemoselective protection of secondary hydroxy group to give a compound of formula

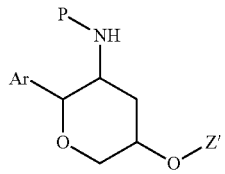
(IXbis)

wherein Z' is a hydroxy protecting group;

h. base-catalyzed cyclization to give a compound of formula (X)

i. deprotection of secondary hydroxy group to give a compound of formula I.

The 2,3,5-substituted tetrahydropyran analogues having the desired configuration are used in the continuation of the reaction aimed to obtain the pharmaceutically active ingredients.

So, 2,3,5-substituted tetrahydropyran of general formula I thus obtained are converted into the corresponding substituted aminotetrahydropyrans dipeptidyl peptidase-IV enzyme inhibitors, particularly omarigliptin, according to techniques that are well known to those skilled in the art.

In primis, a compound of formula I may be converted into its 5-oxo tetrahydropyran analogue of formula Ibis

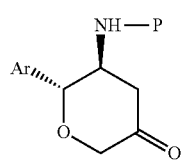

(Ibis)

by reacting with an oxidizing agent in a suitable solvent, for instance, following the teachings described in U.S. Pat. No. 7,902,376.

U.S. Pat. No. 7,902,376 above further describes a way to convert the compound Ibis into the final DPP-4 inhibitors disclosed in WO 2007/126745 as shown in the following scheme

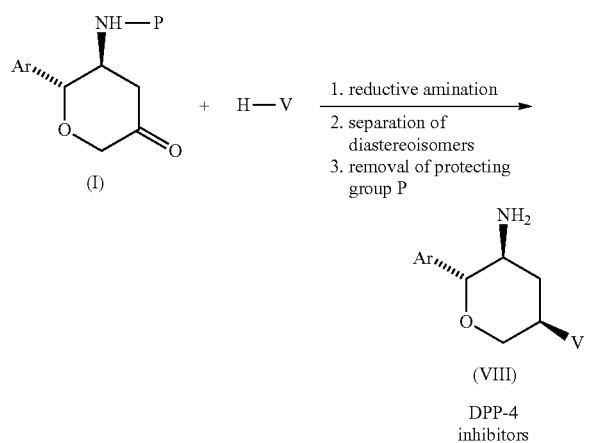

wherein V is defined in said document.

In particular, the synthetic sequence reported above applied to the compound of formula Ibis identified as a separate isomer C2,C3 (2R,3S) gives rise to a final product having the 2R,3S,5R, desired configuration.

When Ar is 2,5-difluorophenyl and V is a 2-(methylsulfonyl)-2,6-dihydropyrrolo[3,4-c]pyrazole, said product constitutes the pharmaceutically active ingredient known as omarigliptin which is reported hereinbelow with the molecular structure and the full stereochemistry

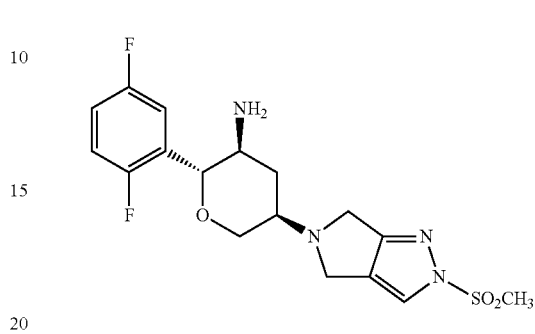

In one embodiment of the invention, omarigliptin is prepared by reductive amination of tetrahydropyranone Ibis with methylsulfonyl-2,6-dihydropyrrolo[3,4-c]pyrazole in the presence of triacetoxyborohydride in a suitable solvent, preferably dimethylacetal to give a protected derivative which is, in turn, deprotected, neutralized and crystallized to give omarigliptin.

Thus, it is a further object of the present invention a process for preparing omarigliptin which comprises the synthesis of a compound of formula I or Ibis as described above. Alternatively, a compound of formula I is directly used in the preparation of the DPP-4 inhibitors.

As mentioned above, the use of a chiral compound of formula II allows fixing the steric configuration of the C5 of the tetrahydropyran ring where pyrrolo[3,4-c]pyrazole moiety is to be inserted.

So, a compound of formula I having desired 2R,3S,5S, configuration is reacted at the hydroxy group at C5, optionally after derivatization to introduce a suitable a leaving group, with a suitable azide or amino reagent through a nucleophilic substitution reaction (SN2 reaction with inversion of the steric configuration of the C5 of the tetrahydropyran ring) that gives rise to an intermediate product having the 2R,3S,5R, desired configuration according to the scheme reported below:

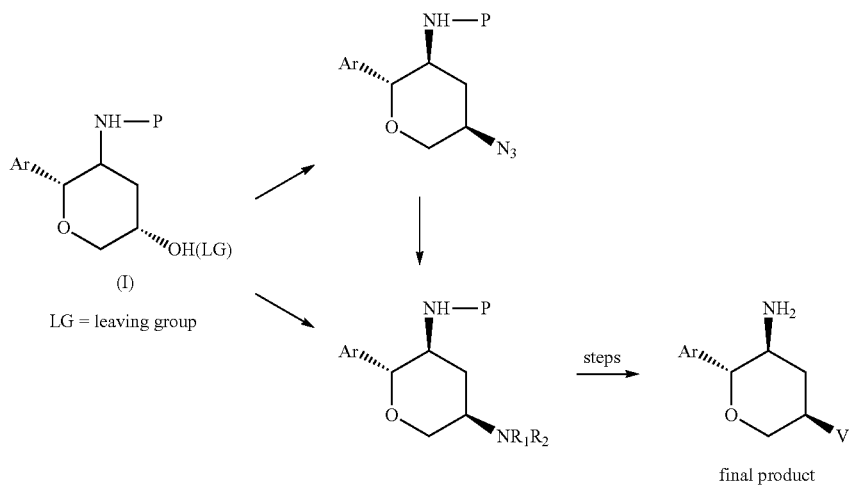

wherein Ar and V are defined as above; said intermediate is, in turn, converted into the desired substituted aminotetrahydropyran dipeptidyl peptidase-IV enzyme inhibitor, particularly omarigliptin, according to techniques that are well known to those skilled in the art.

It is a further object of the present invention a compound of formula

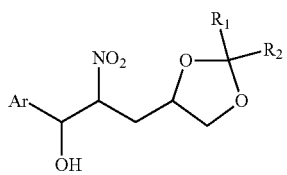

IV wherein Ar is phenyl optionally substituted with one to five R substituent/s each R independently selected from halogen, (C1-C4)-alkyl optionally substituted by halogen, (C1-C4)-alkoxy optionally substituted by halogen; and wherein each $R_1$ and $R_2$ is independently hydrogen and (C1-C4)-alkyl or taken together a (C3-C7)-cycloalkyl group.

It is a further object of the present invention a compound of formula

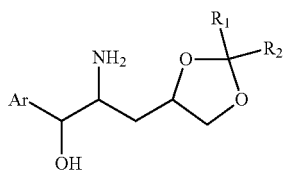

V wherein Ar is phenyl optionally substituted with one to five R substituent/s each R independently selected from halogen, (C1-C4)-alkyl optionally substituted by halogen, (C1-C4)-alkoxy optionally substituted by halogen; and wherein each $R_1$ and $R_2$ is independently hydrogen and (C1-C4)-alkyl or taken together a (C3-C7)-cycloalkyl group.

It is a further object of the present invention a compound of formula

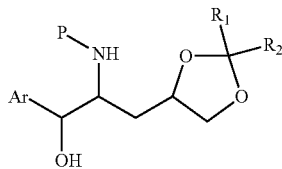

(VI)

wherein Ar is phenyl optionally substituted with one to five R substituent/s each R independently selected from halogen, (C1-C4)-alkyl optionally substituted by halogen, (C1-C4)-alkoxy optionally substituted by halogen; wherein each $R_1$ and $R_2$ is independently hydrogen and (C1-C4)-alkyl or taken together a (C3-C7)-cycloalkyl group; and P is a primary amine protecting group.

It is a further object of the present invention a compound of formula

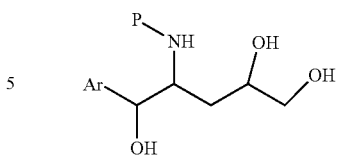

VII wherein Ar is phenyl optionally substituted with one to five R substituent/s each R independently selected from halogen, (C1-C4)-alkyl optionally substituted by halogen, (C1-C4)-alkoxy optionally substituted by halogen; and P is a primary amine protecting group.

It is a further object of the present invention a compound of formula

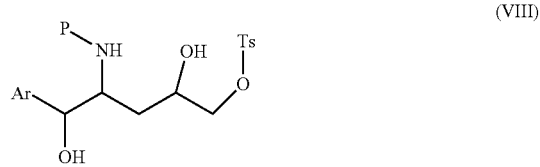

(VIII)

wherein Ar is phenyl optionally substituted with one to five R substituent/s each R independently selected from halogen, (C1-C4)-alkyl optionally substituted by halogen, (C1-C4)-alkoxy optionally substituted by halogen; Ts is a p-toluenesulfonyl (tosyl) group; and P is a primary amine protecting group.

It is a further object of the present invention a compound of formula

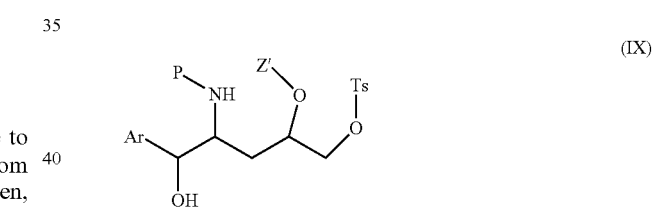

(IX)

wherein Ar is phenyl optionally substituted with one to five R substituent/s each R independently selected from halogen, (C1-C4)-alkyl optionally substituted by halogen, (C1-C4)-alkoxy optionally substituted by halogen; Ts is a p-toluenesulfonyl (tosyl) group; P is a primary amine protecting group; and P' is an hydroxyl protecting group.

It is a further object of the present invention a compound of formula

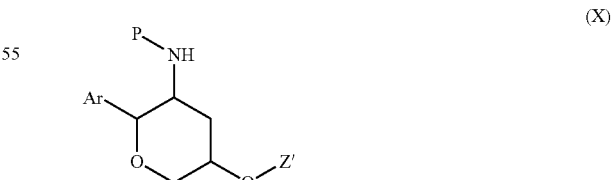

(X)

wherein Ar is phenyl optionally substituted with one to five R substituent/s each R independently selected from halogen, (C1-C4)-alkyl optionally substituted by halogen, (C1-C4)-alkoxy optionally substituted by halogen; P is a primary amine protecting group; and P' is an hydroxy protecting group.

Said compounds of formulae IV, V, VI, VII, VIII, IX and X constitute a further object of the present invention as key intermediates in the preparation of 2,3,5-tetrahydropyran derivatives having the configuration 2R,3S,5R, in particular omarigliptin.

Particularly preferred are compounds of formula:
1-(2,4,5-trifluorophenyl)-2-nitro-3 -((S)-1,4-dioxaspiro[4.5] decan-2-yl)propan-1-ol (IV);
2-amino-1-(2,5-difluorophenyl)-3-((S)-1,4-dioxaspiro[4.5] decan-2-yl)propan-1-ol (V);
2-amino-1-(2,4,5-trifluorophenyl)-3-((S)-1,4-dioxaspiro [4.5]decan-2-yl)propan-1-ol (V);
Benzyl-(1R,2S)-1-(2,5 -difluorophenyl)-1-hydroxy-3-((S)-1,4-dioxaspiro[4.5]decan-2-yl)propan-2-ylcarbamate (VI);
N-((1R,2S)-1-(2,5-difluorophenyl)-1-hydroxy-3-((S)-1,4-dioxaspiro[4.5]decan-2-yl)propan-2-yl)acetamide (VI);
N-((1R,2S,4S)-1-(2,5-difluorophenyl)-1,4,5 -trihydroxypentan-2-yl)acetamide (VII);
Benzyl (1R,2S,4S)-1-(2,5-difluorophenyl)-1,4,5 -trihydroxy-pentan-2-yl-carbamate (VII);
(2S,4S,5R)-4-acetamido-5-(2,5-difluorophenyl)-2,5 -dihydroxypentyl-4-methyl-benzene-sulfonate (VIII);
(2S,4S,5R)-4-(benzyloxycarbonylamino)-5-(2,5-difluorophenyl)-2,5 -dihydroxy-pentyl 4-methylbenzenesulfonate (VIII);
N-((2R,3S,5S)-2-(2,5-difluorophenyl)-5-hydroxytetrahydro-2H-pyran-3-yl)acetamide (I);
N-((2R,3S,5S)-2-(2,5-difluorophenyl)-5-(tetrahydro-2H-pyran-2-yloxy)tetrahydro-2H-pyran-3-yl)acetamide (X); and
Benzyl (1R,2S)-1-(2,5-difluorophenyl)-1-hydroxy-3-((S)-oxiran-2-yl)propan-2-ylcarbamate (XI).

The process according to the invention proposes to simplify the preparation of 2,3,5-substituted tetrahydropyran analogues known as DPP-4 inhibitors and useful in the treatment of type 2 diabetes mellitus.

In particular, the present invention relates to an improved method for synthesizing a di-substituted tetrahydropyran derivative of formula I, intermediate being used in the preparation of active pharmaceutical ingredients via the corresponding nitro derivatives of formula II.

The present invention is characterized by the reaction of a compound of formula II with a compound of formula III to give a nitro aldol compound of formula IV.

To the best of the inventors' knowledge, said nitro-aldol reaction or Henry reaction between a nucleophile generated from a suitable nitroalkane of formula II and an electrophile consisting of a suitable carbonyl compound III according to the invention has never been described or suggested in the prior art.

In particular, the prior art does not describe or suggest both the application of said reaction to the substrates object of the invention and the method for preparing the specific chiral compound of formula II as described and claimed herein.

As above, the main challenge in the preparation of 2,3, 5-substituted tetrahydropyran analogues DPP-4 inhibitors is known to be the effective and practical construction of the correct steric configuration of three chiral centers; contiguous R,S (C2, C3) stereochemical array with an R (C5) functionalized amino group in the tetrahydropyran ring.

First, the present invention is capable of providing a chiral synthon (compound II) containing a nitrogen atom (nitro group) in a simple and efficient manner; in addition, said chiral synthon, via the nitro-aldol reaction described above, allows the direct introduction of the optionally protected hydroxy group into position 5 of the tetrahydropyran ring moiety.

In addition, the desired optical configuration of two O and N bearing contiguous stereogenic centers is established by performing the asymmetric anti-selective nitro-aldol reaction according to the invention in the presence of a catalyst described above.

The resolution of the enriched (2R;3S) diastereoisomeric mixture of a compound of formula IV or V according to known techniques leads to the desired optical isomer.

The picture is completed by high yields, an appreciable reduction in the production costs and the production of a product with an optical and chemical purity such that it can be directly subjected to the subsequent phases of the process.

It is thus evident that the preparation method object of the invention constitutes an efficient and economic synthetic alternative in the preparation of key intermediates in the preparation of pharmaceutical active ingredients; in addition, the ready availability of the starting materials used combined with the reduced number of synthetic steps and the good recorded yields definitely entail appreciable advantages in terms of production costs and efficiency.

A practical embodiment of the process object of the present invention comprises the optional preparation of a nitro derivative of formula II; the reaction of said nitro derivative with a suitable compound of formula III under the Henry conditions to give a compound of formula IV; the conversion of the formula IV lead to the key intermediate of formula I in the preparation of a 2,3,5-substituted tetrahydropyran analogue known as DPP-4 inhibitors.

A preferred practical embodiment of the process object of the present invention comprises the optional preparation of a nitro derivative of formula II via the corresponding aldehyde derivative; the reaction of said nitro derivative with a suitable compound of formula III under the Henry conditions to give a compound of formula IV; the chemoselective reduction of the nitro group of a compound of formula IV and the subsequent protection of the amino group so obtained; diol deprotection; regioselective activation and/or chemoselective hydroxy protection; and base-catalyzed cyclization lead to the key intermediate of formula I; optional oxidation to a compound of formula Ibis, which is converted into omarigliptin according to known techniques.

The relative syn/anti configuration was determined by $^1$H-NMR noesy experiment after derivatization of compound (V) diastereomers with thiophosgene as reported below

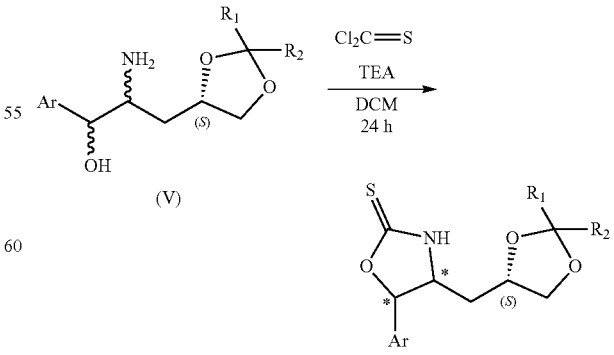

For better illustrating the invention the following examples are now given.

EXAMPLE 1

Synthesis of (R)-1,4-dioxaspiro[4.5]decane-2-carbaldehyde

In a 100 mL single necked round bottom flask, equipped with a magnetic stirrer, 1,2:5,6-Di-O-cyclohexylidene-D-mannitol (5 g; 14,60 mmol) was dissolved in $CH_3CN/H_2O$ (6:4, 25 ml).

The mixture was cooled to 0° C. with an external ice bath and $NaIO_4$ (6.246 g; 29.20 mmol) was added in portions over a period of 30 min. The resulting mixture was allowed to warm to room temperature and stirred for 2 hours.

After the reaction time, a precipitate was filtered and washed with $CH_3CN/H_2O$. The solvent was removed under vacuum and title compound was obtained as a clear oil without any further purification (26 mmol; 89% yield).

EXAMPLE 2

Synthesis of (S)-2-(2-nitroethyl)-1,4-dioxaspiro[4.5]decane (II)

Step (i): 2-nitro-1-((R)-1,4-dioxaspiro[4.5]decan-2-yl)ethanol

In a 100 mL two necked round bottom flask, equipped with a mechanic stirrer, $CH_3NO_2$ (1.65 g; 27 mmol) was added to a solution of Example 1 compound (4.435 g; 26 mmol) in EtOH (12 ml).

The mixture was cooled to 0° C. with an external ice bath and aq. 10% NaOH solution (2.6 ml; 1.04 g NaOH, 26 mmol) was added dropwise. The resulting mixture was stirred for 30 min, then allowed to warm to room temperature and stirred overnight. Subsequently, $CH_3COOH$ (1.56 g; 26 mmol) was added.

The product was extracted with $Et_2O$ and the organic layer was washed two times with distilled water. The organic phase was then dried over $Na_2SO_4$ and the solvent removed under vacuum.

The crude was purified by flash column chromatography on silica gel (eluent:

Hexane/AcOEt=7/3) to yield a clear oil (19.5 mmol; 75% yield).

TLC: Rf=0,37 (Hexane/AcOEt=7/3)

Step (ii): (S)-2-(2-nitrovinyl)-1,4-dioxaspiro[4.5]decane

In a 100 mL 2 necked round bottom flask, equipped with a magnetic stirrer and a nitrogen inlet tube, dry triethylamine (2.543 g; 25.18 mmol) was added to a solution of step (i) product (4.5 g; 19.46 mmol) in dry DCM (19 ml).

The mixture was cooled to 0° C. with an external ice bath and MsCl (2.441 g; 21.31 mmol) was added dropwise.

The resulting mixture was allowed to warm to room temperature and stirred under inert atmosphere for 2 hours. The reaction was quenched with sat. aq. $Na_2CO_3$.

The organic phase was separated and aqueous phase extracted two times with DCM.

The combined organic phases were washed with brine and dried over $Na_2SO_4$; the solvent removed under vacuum to afford the product in quantitative yield (19.37 mmol).

TLC: Rf=0.55 (Hexane/AcOEt=9/1)

$^1$H-NMR (300 MHz, $CDCl_3$): δ 7.24 (s, 2H); 4.82 (dd, 1H); 4.29 (dd, 1H); 3.79 (dd, 1H); 1.75-1.65 (m, 8H); 1.48 (m, 2H).

Step (iii): title compound (II)

In a 25 mL two necked round bottom flask, fitted with a magnetic stirrer, a reflux condenser and a nitrogen inlet tube, N,N'-diphenylthiourea (164 mg; 0.72 mmol) and Hantzsch ester (1.996 g; 7.88 mmol) were sequentially added to a solution of step (ii) product (1.535 g; 7.2 mmol) in dry DCM (7 ml).

The solution was stirred at reflux under inert atmosphere for 24 h. The solvent was evaporated under controlled vacuum (200 mbar) and the crude was purified by flash column chromatography (eluent: $CH_2Cl_2$/MeOH=99/1).

Title Compound was isolated as a brownish oil (5.54 mmol; 79% yield).

TLC: Rf=0.54 ($CH_2Cl_2$)

$^1$H-NMR (300 MHz, $CDCl_3$): δ 4.61 (dd, 2H); 4.21 (m, 1H); 4.13 (dd, 1H); 3.63 (dd, 1H); 2.34 (m, 1H); 2.17 (m, 1H); 1.65-1.55 (m, 8H); 1.40 (m, 2H).

EXAMPLE 2bis

Synthesis of (S)-2,2-dimethyl-4-(2-nitroethyl)-1,3-dioxolane

Starting from 1,2:5,5-di-O-isopropiliden-D-mannitol and by following procedures described in Examples 1 and 2, the title compound (S)-2,2-dimethyl-4-(2-nitroethyl)-1,3-dioxolane was prepared in a 80-90% yield via intermediates (R)-2,2-dimethyl-1,3-dioxolane-4-carbaldehyde, 1-((R)-2,2-dimethyl-1,3-dioxolan-4-yl)-2-nitroethanol and (S,E)-2,2-dimethyl-4-(2-nitrovinyl)-1,3-dioxolane.

EXAMPLE 3

Synthesis of 1-(2,5-difluorophenyl)-2-nitro-3-((S)-1,4-dioxaspiro[4.5]decan-2-yl)propan-1-ol (IV): diastereomeric mixture at C1, C2 with anti-diastereomer-(1R,2S) as major product In a 250 mL 2 necked round bottom flask, equipped with a magnetic stirrer and a nitrogen inlet tube, the chiral complex of Cu(II) was prepared in situ by addition of $Cu(OTf)_2$ (20 mg; 0.056 mmol) to a solution L-(−)-camphor-derived aminopyridine ligand (Ligand F) (16 mg; 0.067 mmol) in dry dioxane (4 mL).

After 30 min, the mixture was cooled to 4° C. with an external ice water bath and triethylamine (11 mg, 0.11 mmol) was added.

A solution of Example 2 compound [Compound (II)] (1.198 g; 5.56 mmol) in dry dioxane (1.5 mL), prepared under nitrogen atmosphere, was added; subsequently, 2,5-difluorobenzaldehyde Compound (III) (157 mg; 1.05 mmol) was added dropwise.

The resulting mixture was allowed to warm to room temperature and stirred under inert atmosphere for 48 hours.

The mixture was concentrated and then diluted in 3 mL of EtOAc. The organic layer was washed three times with 3 mL of distilled water. The organic phase was dried over $Na_2SO_4$ and the solvent was removed under vacuum.

The crude was purified by flash column chromatography (eluent: $CH_2Cl_2$ 200 mL, $CH_2Cl_2$/MeOH=99/1 400 mL, $CH_2Cl_2$/MeOH=98/2 400 mL).

The following fractions were obtained:

Starting material Compound (II) recovered as a clean product=635 mg

Title compound (IV) (mix of all 4 diastereomers)=472 mg (conversion >95%)

TLC: Rf=0.23 ($CH_2Cl_2$)

The diastereoisomeric excess was determined by HPLC on chiral stationary phase (Chiralpack IB, flow 1 mL/min, pressure 39 bar, Hexane/2-Propanol=98/2).

Diastereomeric ratio: 45/10/14/31

Compound (IV), major diastereomer: anti-diastereomer-(1R,2S)

$^1$H-NMR (300 MHz, CDCl$_3$): δ 7.26 (m, 1H); 7.04 (m, 2H); 5.71 (bs, 1H); 5.05 (ddd, 1H); 4.21 (dd, 1H); 3.60 (dd, 1H); 3.55 (m, 1h); 2.35 (m, 1H); 1.76 (m, 1H); 1.65-1.55 (m, 8H); 1.40 (m, 2H).

EXAMPLE 3bis

Synthesis of 1-(2,5-difluorophenyl)-2-nitro-3-((S)-1,4-dioxaspiro[4.5]decan-2-yl)propan-1-ol (IV)

By following procedures described in Example 3, nitro aldol reaction of a compound of formula II, Example 2 compound, with a compound of formula III, 2,5-difluorobenzaldehyde, to give title compound of formula IV was performed in the presence of ligand F exploring different experimental conditions, stoichiometry, solvents, temperature, copper salts, etc., resulting in a 55-75% yield; data are reported in Table 1 below:

TABLE 1

| Entry | Solvent | Temperature | Catalyst | Time | Diastereoisomers |
|---|---|---|---|---|---|
| 1 | Dioxane | 0 | Cu(OTf)$_2$ 5% in mol | 24 h | 35/10/30/23 |
| 2 | EtOH | RT | Cu(OTf)$_2$ 5% in mol | 24 h | 33/10/37/19 |
| 3 | Dioxane | 24 h ° C.; 24 h RT | Cu(OTf)$_2$ 5% in mol | 48 h | 47/8/20/25 |
| 4 | Dioxane | RT | Cu(OTf)$_2$ 5% in mol | 60 h | 55/9/11/25 |
| 5 | Dioxane | RT | Cu(OTf)$_2$ 5% in mol | 24 h | 40/10/25/25 |
| 6 | EtOH | RT | Cu(AcO)$_2$•H$_2$O 5% in mol | 24 h | 27/10/39/24 |
| 7 | EtOH | RT | Cu(AcO)$_2$•H$_2$O 5% in mol | 6 h | 36/12/33/19 |
| 8 | Dioxane | RT | Cu(OTf)$_2$ 10% in mol | 24 h | 31/11/36/21 |
| 9 | Dioxane | 5 | Cu(OTf)$_2$ 5% in mol | 24 h | 32/11/36/21 |

Entry 9 was repeated by using Cu(OAc)$_2$ (0.05 eq.) in the presence of ligand B (0.06 eq) as catalyst to give a compound of formula IV in 80% yield (diastereoisomers rate 28:15:7:50). The diastereomeric ratio was determined in the nitro aldol of general formula IV by HPLC on chiral stationary phase.

EXAMPLE 3ter

Synthesis of 1-(2,4,5-trifluorophenyl)-2-nitro-3-((S)-1,4-dioxaspiro[4.5]decan-2-yl)propan-1-ol (IV)

By following procedures described in Example 3, nitro aldol reaction of a compound of formula II, Example 2 compound, with 2,4,5-trifluorobenzaldeyde of formula III to give title compound of formula IV was performed in the presence of copper diacetate Cu(OAc)$_2$ (0.05 eq.) with a chiral ligand (0.06 eq); results obtained by exploring different ligands, solvents and temperatures (reaction time 24h) are reported in Table 2 below:

TABLE 2

| entry | ligand | temp (° C.) | solvent | (1S,2R):(1R,2R): (1R,2S):(1S,2S) | yield (%) |
|---|---|---|---|---|---|
| 1 | A | rt | dioxane:THF (85:15) | 13:32:24:31$^+$ | 85 |
| 2 | A | +5 | dioxane:THF (85:15) | 14:35:5:46 | 84$^+$ |
| 3 | B | +5 | Dioxane:THF (85:15) | 27:13:10:59 | 83 |
| 4 | B | −10 | THF | 5:39:3:52 | 20 |
| 5** | B | +5 | dioxane | 17:18:25:40$^+$ | >99 |
| 6 | C | +5 | dioxane:THF (85:15) | 27:25:21:27 | 10$^+$ |
| 7 | C | −10 | THF | 31:21:22:26 | 16 |
| 8 | D | +5 | dioxane | 34:15:12:39 | 80$^+$ |
| 9 | E | +5 | dioxane | 7:9:60:24 | 60$^+$ |

EXAMPLE 3quater

Synthesis of 1-(2,5-difluorophenyl)-2-nitro-3-((S)-1,4-dioxaspiro[4.5]decan-2-yl)propan-1-ol (IV): diastereomeric mixture at C1, C2 with anti-diastereomer-(1R,2S) as major product In a 250 mL 2 necked round bottom flask, equipped with a magnetic stirrer and a nitrogen inlet tube, a solution of quinidine derivative ligand G (60 mg; 0.099 mmol) in dry THF (3 mL) was added to Cu(OTf)$_2$ (36 mg; 0.099 mmol). After 1 hour, a solution of Example 2 compound [Compound (II)] (2.133 g; 9.86 mmol) in dry THF (1.0 mL), prepared under nitrogen atmosphere, was added; subsequently, 2,5-difluorobenzaldehyde Compound (III) (280 mg; 1.97 mmol) was added dropwise. The mixture was cooled to −20° C. with an external ice water bath and triethylamine (11 mg, 0.99 mmol) was added. The resulting mixture was stirred at −20° C. under inert atmosphere for 24 hours. The reaction was quenched with 250 microL of HCl solution (10% in water) and stirred for 5 minutes; then, diluted in 10 mL of EtOAc and 10 ml of water. The organic phase was separated and the aqueous phase extracted three times with EtOAc. The combined organic phases was dried over Na$_2$SO$_4$ and the solvent was removed under vacuum to give 2.5 g of crude. The crude was purified by flash column chromatography (eluent: CH$_2$Cl$_2$/MeOH=99/1).

The following fractions were obtained:
Starting material Compound (II) recovered as a clean product=1.750 g
Title compound (IV) (mix of all 4 diastereomers)=694 mg (conversion 98%)
TLC: Rf=0.23 (CH$_2$Cl$_2$)
The diastereoisomeric excess was determined by HPLC on chiral stationary phase (Chiralpack IB, flow 1 mL/min, pressure 39 bar, Hexane/2-Propanol=98/2).
Diastereomeric ratio: 55/23/12/10
Compound (IV), major diastereomer: anti-diastereomer-(1R,2S)
$^1$H-NMR (300 MHz, CDCl$_3$): δ 7.26 (m, 1H); 7.04 (m, 2H); 5.71 (bs, 1H); 5.05 (ddd, 1H); 4,21 (dd, 1H); 3.60 (dd, 1H); 3.55 (m, 1h); 2.35 (m, 1H); 1.76 (m, 1H); 1.65-1.55 (m, 8H); 1.40 (m, 2H).

To note that purification of major isomer (as amino alcohol after hydrogenation) resulted to be easier because of the low content (10) of minor isomer.

EXAMPLE 4

Synthesis of 2-amino-1-(2,5-difluorophenyl)-3-((S)-1,4-dioxaspiro[4.5]decan-2-yl)propan-1-ol (V), anti-diastereomer isolated as major product: (1R,2S)-2-amino-1-(2,5-difluorophenyl)-3-((S)-1,4-dioxaspiro[4.5]decan-2-yl)propan-1-ol A reactor, equipped with a magnetic stirrer, was charged with Example 3 compound [Compound (IV) mix of all 4 diastereomers] (458 mg, 1.28 mmol), 5% Pd/C (50% solution in water; 273 mg 6.8 mg Pd, 0.064 mmol) in MeOH (6 ml). The reactor was introduced in an autoclave and it was subjected to $H_2$ pressure (25 atm). The mixture was stirred at room temperature overnight. The catalyst was removed by filtration and the solvent was removed under vacuum to give crude product Compound (V) as a mix of all 4 diastereomers. The diastereoisomers were separated by flash column chromatography (eluent: $CH_2Cl_2/MeOH=95/5+0.5\%$ TFA); two out of the four possible diastereoisomers were obtained:
Compound (V) syn-diastereomer: 40 mg, and
Compound (V) anti-diastereomer-(1R,2S): 97 mg.
TLC: Rf=0.38 and 0.39 ($CH_2Cl_2/MeOH=1/1$)
Compound (V), anti-diastereomer-(1R,2S)
$^1$H-NMR (300 MHz, $CDCl_3$): δ 7.24 (m, 1H); 6.96 (m, 2H); 4.97 (d, 1H); 4.24 (m, 1H); 4.00 (dd, 1H); 3.48 (dd, 1H); 3.36 (m, 1H); 2.66 (bs, 2H); 1.65-1.50 (m, 10H); 1.37 (m, 2H).

EXAMPLE 4bis

Synthesis of 2-amino-1-(2,4,5-trifluorophenyl)-3-((S)-1,4-dioxaspiro[4.5]decan-2-yl)propan-1-ol (V)

Starting from a compound of formula IV obtained in Example 3ter, by following procedures described in Examples 4, the title compound 2-amino-1-(2,4,5-trifluorophenyl)-3-((S)-1,4-dioxaspiro[4.5]decan-2-yl)propan-1-ol (V) was prepared in a 90% yield.

EXAMPLE 5

Synthesis of benzyl (1R,2S)-1-(2,5-difluorophenyl)-1-hydroxy-3-((S)-1,4-dioxaspiro[4.5]decan-2-yl)propan-2-ylcarbamate (VI): P=Cbz In a 5 mL 2 necked round bottom flask, equipped with a magnetic stirrer and a nitrogen inlet tube, dry triethylamine (60.6 mg; 0.60 mmol) was added to a solution of Example 4 compound [Compound (V) anti-diastereomer-(1R,2S)] (97 mg; 0.30 mmol) in dry THF (1 ml). The mixture was cooled to 0° C. with an external ice bath and benzyl chloroformate (75 mg; 0.44 mmol) was added dropwise. The resulting mixture was allowed to warm to room temperature and stirred under inert atmosphere for 18 hours. EtOAc and $H_2O$ were added; the organic phase was separated and the aqueous phase extracted two times with EtOAc. The combined organic phases were washed with brine end then was dried over $Na_2SO_4$. The solvent was removed under controlled vacuum to obtain 130 mg of crude product which was purified by flash column chromatography on silica gel (eluent: Hexane/AcOEt=8/2). Title compound was isolated as a clear oil (0.18 mmol; 60% yield).
TLC: Rf=0,21 (Hexane/AcOEt=8/2)
$^1$H-NMR (300 MHz, $CDCl_3$): δ 7.40-7.26 (m, 5H); 7.24 (m, 1H); 6.96 (m, 2H); 5.41 (bd, 1H); 5.20 (bs, 1H); 5.15 (s, 2H); 4.24 (dd, 1H); 4.19 (m, 1H); 4.01 (dd, 1H); 3.52 (dd, 1H); 1.76 (m, 1H); 1.68-1.48 (m, 9H); 1.35 (m, 2H).

EXAMPLE 6

Synthesis of N-((1R,2S)-1-(2,5-difluorophenyl)-1-hydroxy-3-((S)-1,4-dioxaspiro[4.5]decan-2-yl)propan-2-yl)acetamide (VI): P=Acetyl In a 25 mL 2 necked round bottom flask, equipped with a magnetic stirrer and a nitrogen inlet tube, dry triethylamine (297 mg; 2.94 mmol) was added to a solution of Compound (V) [anti-diastereomer-(1R,2S)] (162 mg; 0.49 mmol) in dry THF (5 ml). The mixture was cooled to 0° C. with an external ice bath and acetyl chloride (154 mg; 1.97 mmol) was added dropwise. The resulting mixture was allowed to warm to room temperature and stirred under inert atmosphere for 18 hours. EtOAc and $H_2O$ were added; the organic phase was separated the aqueous phase was extracted two times with EtOAc. The combined organic phases were washed with brine and dried over $Na_2SO_4$; the solvent was removed under vacuum to obtain 200 mg of crude product which was purified by flash column chromatography on silica gel (eluent: Hexane/EtOAc=7/3). Title compound was isolated as a clear oil (0.34 mmol; 70% yield).
TLC: Rf=0.16 (Hexane/AcOEt=7/3)
$^1$H-NMR (300 MHz, $CDCl_3$):
δ 7.30 (m, 1H); 6.96 (m, 2H); 5.20 (d, 1H); 4.30-4.10 (m, 2H); 4.02(dd, 1H); 3.52 (ddd, 1H); 2 (s, 3H); 1.72 (m, 1H), 1.65-1.50 (m, 9H); 1.37 (m, 2H).

EXAMPLE 7

Synthesis of N-((1R,2S,4S)-1-(2,5-difluorophenyl)-1,4,5-trihydroxypentan-2-yl)acetamide (VII): P=Acetyl In a 10 mL one necked round bottom flask, equipped with a magnetic stirrer, Example 6 compound (91 mg; 0.25 mmol) was dissolved in THF (1 ml). The mixture was cooled to 0° C. with an external ice bath and aq. HCl (2.7 M; 1 ml) was added dropwise.
The resulting mixture was allowed to warm to room temperature and stirred for 8 hours. The reaction was then quenched with $NaHCO_3$ aqueous solution; the organic phase was separated the aqueous phase was extracted three times with EtOAc. The combined organic phases were dried over $Na_2SO_4$ and concentrated under vacuum to obtain 73 mg of crude.
The product was purified by flash column chromatography on silica gel (eluent: $CH_2Cl_2/MeOH=95/5$).
Title compound was isolated as a clear oil (0.16 mmol; 64% yield).
TLC: Rf=0.13 ($CH_2Cl_2/MeOH=95/5$)
$^1$H-NMR (300 MHz, $CDCl_3$):
δ 7.27 (m, 1H); 7.04 (m, 2H); 5.06 (d, 1H); 4.38 (m, 1H); 3.62(m, 1H); 3.44 (dd, 1H); 3.36 (m, 2H); 1.91 (s, 3H); 1.62 (ddd, 2H).

EXAMPLE 8

Synthesis of (2S,4S,5R)-4-acetamido-5-(2,5-difluorophenyl)-2,5-dihydroxypentyl 4-methylbenzenesulfonate (VIII): P=Acetyl In a vial, equipped with a magnetic stirrer, Example 7 compound (47 mg; 0.16 mmol) and $Bu_2SnO$ (2 mg; 0.008 mmol) were suspended in $CH_2Cl_2$ (1 ml) and TEA (18 mg; 18 mmol) were added. The mixture was cooled to 0° C. with an external ice bath and p-toluensulfonyl chloride (TsCl) (34 mg; 0.18 mmol) was added in small portions.
The resulting mixture was allowed to warm to room temperature and was stirred for 18 hours. The catalyst was then removed by filtration the solvent was evaporated under vacuum to obtain 75 mg of crude product.

The product was purified by flash column chromatography on silica gel (eluent: $CH_2Cl_2$/MeOH=99/1). Title compound was isolated as a clear oil (0.07 mmol; 43% yield).
TLC: Rf=0.28 ($CH_2Cl_2$/MeOH=98/2)
$^1$H-NMR (300 MHz, $CDCl_3$):
δ 7.76 (d, 2H); 7.35 (d, 2H); 7.20 (m, 1H); 6.98 (m, 2H); 6.37 (d, 2H); 5.18 (d, 1H); 4.34 (m, 1H); 3.92-3.80 (m, 3H); 2.46 (s, 3H); 2.06 (s, 3H); 1.65 (ddd, 1H); 1.31 (ddd, 1H).

EXAMPLE 9

Synthesis of N-((2R,3 S,5 S)-2-(2,5-difluorophenyl)-5-hydroxytetrahydro-2H-pyran-3-yl)acetamide (I): P=Acetyl in mixture with N-((2R,3S,5S)-2-(2,5-difluorophenyl)-5-(tetrahydro-2H-pyran-2-yloxy)tetrahydro-2H-pyran-3-yl)acetamide (X): with P=Acetyl, Z'=THP In a vial, equipped with a magnetic stirrer, a solution of Example 8 compound (20 mg; 0.045 mmol), 3,4-dihydropyran (15 mg; 0.18 mmol) and p-TsOH.$H_2O$ (2 mg; 0.011 mmol) in dry $CH_2Cl_2$ (0.5 ml) was prepared under $N_2$ atmosphere. The mixture was stirred over 4 hours at room temperature and then the solvent was removed under vacuum. The crude product was directly used in the next step.

In a 10 mL 2 necked round bottom flask, equipped with a magnetic stirrer and a nitrogen inlet tube, NaH (50% in mineral oil, 15 mg; 0.31 mmol) was washed by pentane three time. Dry THF (1 mL) was added, then the mixture was cooled to 0° C. with an external ice bath and a solution of the previously obtained crude compound in THF (1 mL) was added dropwise. The resulting mixture was allowed to warm up to room temperature and stirred for 48 hours. After that a 1 M HCl solution (2 mL) was added and the mixture was stirred for 18 hours. The reaction was diluted with EtOAc, the organic phase was separated and the aqueous phase was extracted two times with EtOAc. The combined organic phases were dried over $Na_2SO_4$ and the solvent was removed under vacuum to obtain 10 mg of crude.

The crude mixture was passed through a plug of silica gel (eluent: $CH_2Cl_2$/MeOH=98/2) obtaining an isolated fraction of pure product.

LC-MS analysis of the isolated fraction showed the following peaks:
Mass (ESI+) m/z=272 [M+H]$^+$ corresponding to the desired product Compound (I); P=Ac
Mass (ESI+) m/z=356 [M+H]$^+$ corresponding to the cyclised product still protected at the hydroxyl group Compound (X); P=Ac, P'=THP

EXAMPLE 10

Synthesis of benzyl (1R,2S,4S)-1-(2,5-difluorophenyl)-1,4,5-trihydroxy-pentan-2-yl-carbamate (VII): P=Cbz In a 10 mL one necked round bottom flask, equipped with a magnetic stirrer, Example 5 compound (97 mg; 0.26 mmol) was dissolved in THF (1 ml). The mixture was cooled to 0° C. with an external ice bath and diluted HCl (2.7 M; 1 ml) was added dropwise.

The resulting mixture was allowed to warm to room temperature and stirred for 8 hours. The reaction was then quenched with NaHCO3 aqueous solution. The organic phase was separated and the aqueous phase extracted three times with EtOAc. The combined organic phases were dried over Na2SO4 and the solvent was removed under vacuum to obtain 100 mg of crude.

The product was purified by flash column chromatography on silica gel (eluent: CH2Cl2/MeOH=95/5). Title compound was isolated as a clear oil (0.20 mmol; 77% yield).
TLC: Rf=0.20 (CH2Cl2/MeOH=95/5)
1H-NMR (300 MHz, CDCl3):
δ 7.40-7.26 (m, 5H); 7.23 (m, 1H); 6.98 (m, 2H); 5.35 (bd, 1H); 5.13 (bs, 3H); 5.15 (s, 2H); 4.13 (m, 1H); 3.77 (m, 1H); 3.63 (ddd, 1H); 3.48 (ddd, 1H); 1.86 (m, 1H); 1.5 (m, 1H).

EXAMPLE 11

Synthesis of (2S,4S,5R)-4-(benzyloxycarbonylamino)-5-(2.5-difluorophenyl)-2,5-dihydroxypentyl 4-methylbenzenesulfonate (VIII): P=Cbz In a vial, equipped with a magnetic stirrer, Example 10 compound (70 mg; 0.18 mmol) and Bu2SnO (1 mg; 0.004 mmol) were suspended in CH2Cl2 (1 ml) and TEA (18 mg; 0.18 mmol) was added.

The mixture was cooled to 0° C. with an external ice bath and TsCl (34 mg; 0.18 mmol) was added in small portions.

The resulting mixture was allowed to warm to room temperature and stirred for 18 hours.

The catalyst was then removed by filtration and the solvent was removed under vacuum to obtain 118 mg of crude.

The product was purified by flash column chromatography on silica gel (eluent:
CH2Cl2/MeOH=95/5). Title compound was isolated as a clear oil (0.09 mmol; 50% yield).
Rf=0.84 (CH2Cl2/MeOH=95/5)
1H-NMR (300 MHz, CDCl3):
δ 7.80 (dd, 2H); 7.40-7.21 (m, 7H); 6.96 (m, 2H); 5.41 (bd, 0.4H); 5.30 (bd, 0.6H); 5.18 (bs, 0.4H); 5.11 (s, 0.8H); 5.08 (bs, 0.60); 5.00 (s, 1.2H); 4.16 (m, 1H); 3.93 (m, 1H); 3.65 (m, 1H); 3.21 (bs, 0.6H); 3.07 (bs, 0.4); 2.45 (s, 3H); 1.86-1.54 (m, 2H).

EXAMPLE 12

Synthesis of benzyl (1R,2S)-1-(2,5-difluorophenyl)-1-hydroxy-3-((S)-oxiran-2-yl)propan-2-ylcarbamate (XI): P=Cbz In a 25 mL 2 necked round bottom flask, equipped with a magnetic stirrer and a nitrogen inlet tube, NaH (50% in mineral oil; 6 mg; 0.129 mmol) was washed by pentane three times. Dry THF (1 mL) was added, then the mixture was cooled to 0° C. with an external ice bath and solution of Example 11 compound (46 mg; 0.086 mmol) in THF (1 mL) was added dropwise.

The resulting mixture was allowed to warm to room temperature and stirred for 18 hours. The reaction was then quenched with NH4Cl aqueous s.s.; the organic phase was separated the aqueous phase was extracted two times with EtOAc. The combined organic phases were dried over Na2SO4 and concentrated under vacuum to obtain 36 mg of crude.

The product was purified by flash column chromatography on silica gel (eluent: Hexane/EtOAc=7:3). Title compound was isolated as a clear oil (0.026 mmol; 31% yield) and 22 mg of Example 11 compound was recovered.
Rf=0.17 (Hexane/EtOAc=6:4)
1H-NMR (300 MHz, DMSO, 330K):

δ 7.35-7.09 (m, 8H); 4.95 (d, 2H); 4.90 (m, 1H); 3.92(m, 1H); 2.89 (m, 1H); 2.65 (m, 1H); 2.47 (m, 1H); 1.70 (m, 2H).

EXAMPLE 13

Synthesis of (1R,2S)-2-acetamido-1-(2,5-difluorophenyl)-3-((S)-1,4-dioxaspiro[4.5]decan-2-yl)propyl acetate (VIbis): P=Acetyl; W=Acetyl In a 5 mL one necked round bottom flask, equipped with a magnetic stirrer and under nitrogen atmosfere, a mixture 1:1 pyridine/Ac2O (0.5 ml) was added to Compound (V) [anti-diastereomer-(1R,2S)] (120 mg; 0.37 mmol) cooling at 0° C.

The resulting mixture was allowed to warm to room temperature and stirred under inert atmosphere for 18 hours. EtOAc and H2O were added; the organic phase was separated the aqueous phase was extracted two times with EtOAc. The combined organic phaseswere washed with brine and dried over Na2SO4; the solvent was removed under vacuum to obtain 157 mg of crude. The product was purified by flash column chromatography on silica gel (eluent: Hexane/EtOAc=7/3). Title compound was isolated as a clear oil (0.29 mmol; 77% yield).

TLC: Rf=0.18 (Hexane/AcOEt=1/1)
$^1$H-NMR (300 MHz, CDCl$_3$):
δ 7.08 (m, 1H); 6.99 (m, 2H); 6.17 (d, 1H); 6.10 (d, 1H); 4.63 (m, 1H); 4.28 (m, 2H); 4.05(dd, 1H); 3.51 (dd, 1H); 2.15 (s, 3H);1.87 (s, 3H); 1.85-1.80 (m, 2H), 1.65-1.50 (m, 8H); 1.44-1.40 (m, 2H).

EXAMPLE 14

Synthesis of (1R,2S,4S)-2-acetamido-1-(2,5-difluorophenyl)-4,5-dihydroxypentyl acetate (VIIbis): P=Acetyl; W=Acetyl In a 10 mL one necked round bottom flask, equipped with a magnetic stirrer, compound VIbis (140 mg; 0.34 mmol) was added and it was dissolved in THF (1 ml). The mixture was cooled to 0° C. with an external ice bath and HCl solution (1 ml; 2.7 M) was added dropwise. The resulting mixture was allowed to warm to room temperature and stirred for 8 hours. The reaction was then quenched with NaHCO$_3$ aqueous solution; the organic phase was separated the aqueous phasewas extracted three times with EtOAc. The combined organic phases were dried over Na$_2$SO$_4$ and concentrated under vacuum to obtain 144 mg of crude.

The product was purified by flash column chromatography on silica gel (eluent: CH$_2$Cl$_2$/MeOH=95/5). Title compound was isolated as a clear oil (0.24 mmol; 71% yield).

TLC: Rf=0.32 (CH$_2$Cl$_2$/MeOH=9/1)
$^1$H-NMR (300 MHz, CDCl$_3$):
δ 7.03 (m, 3H); 6.20 (d, 1H); 6.06 (d, 1H); 4.55 (m, 1H); 3.65 (m, 1H); 3.49 (m, 2H); 2.18 (s, 3H); 1.91 (s, 3H); 1.63 (m, 1H); 1.40 (m, 1H).

EXAMPLE 15

Synthesis of (1R,2S,4S)-2-acetamido-1-(2,5-difluorophenyl)-4-hydroxy-5-(tosyloxy)pentyl acetate (VIIIbis): P=Acetyl; W=Acetyl In a vial, equipped with a magnetic stirrer,compound VIIbis (78 mg; 0.24 mmol) and Bu$_2$SnO (3 mg; 0.012 mmol) were suspended in CH$_2$Cl$_2$ (1 ml) and TEA (24 mg; 0.24 mmol) were added. The mixture was cooled to 0° C. with an external ice bath and TSCl (45 mg; 0.24 mmol) was added in small portions.

The resulting mixture was allowed to warm to room temperature and was stirred for 18 hours. The catalyst wasthen removed by filtration the solvent was evaporated under vacuum to obtain 108 mg of product (0.22 mmol; 92% yield), that was used in the next step without further purification.

TLC: Rf=0.22 (CH$_2$Cl$_2$/MeOH=98/2)
$^1$H-NMR (300 MHz, CDCl$_3$):
δ 7.78 (d, 2H); 7.42 (d, 2H); 6.99 (m, 3H); 6.37 (d, 2H);5.18 (d, 1H); 4.34 (m, 1H); 3.92-3.80 (m, 3H); 2.46 (s, 3H); 2.06 (s, 3H); 1.65 (ddd, 1H); 1.31 (ddd, 1H).

EXAMPLE 16

Synthesis of (1R,2S,4S)-2-acetamido-1-(2,5-difluorophenyl)-4-(tetrahydro-2H-pyran-2-yloxy)-5-(tosyloxy)pentyl acetate (IXbis): P=Acetyl; Z'=THP W=Acetyl In a 5 mL, one necked-round bottom flask, equipped with a magnetic stirrer,a solution of compound VIIIbis (108 mg; 0.22 mmol), 3,4-dihydropyran (112 mg; 1.36 mmol) and p-TsOH (4.2 mg; 0.022 mmol) in dry CH$_2$Cl$_2$ (2 ml) was prepared under N$_2$ atmosfere. The mixture was stirred for 5 hours at room temperature and then the solvent was removed under vacuum. The crude reaction mixture was purified by flash column chromatography on silica gel (eluent: CH$_2$Cl$_2$/MeOH=99/1).

Two fractions (ratio 50/50) were obtained and analysed by $^1$H-NMR; they were supposed to be two diasteroisomers formed by protective group and therefore riunited (IXbisA)

When 20 equivalents of DHP and 5 hours only as reaction time were used only one major product was obtained (65% yield, r.d. ratio 87/13) (IXbisB).

EXAMPLE 17

Synthesis of N-((2R,3S,5S)-2-(2,5-difluorophenyl)-5-hydroxytetrahydro-2H-pyran-3-yl)acetamide (I): P=Acetyl Compound IXbis (119 mg; 0.21 mmol) was placed into a round bottom flask and was dissolved in MeOH (1 mL) and K2CO3 s.s. was added (1 mL). The mixture was stirred 18 h at rt. After concentration and extraction with AcOEt the crude was used in the following step without further purification.

In a 10 mL, 2 necked-round bottom flask, equipped with a magnetic stirrer and a nitrogen inlet tube, NaH (25 mg; 0.63 mmol) was washed with pentane three times. Dry THF (0.5 mL) was added, then the mixture was cooled to 0° C. with an external ice bath and a solution of the crude previously obtained in THF (0.5 mL) was added dropwise.

The resulting mixture was allowed to warm up to room temperature and stirred for 24 hours. The reaction was quenched with H$_2$O and diluted with EtOAc; the phases were separated and the aqueous phase was extracted three times with EtOAc. The combined organic phases were dried over Na$_2$SO$_4$ and concentrated under vacuum to obtain 21 mg of crude, that was used in the next step without further purification.

In a 5 mL, one necked-round bottom flask, equipped with a magnetic stirrer, a solution of the crude previously obtained in THF was prepared and then a 1 M HCl solution (1 mL) was added. The mixture was stirred for 18 hours at room temperature. The reaction was diluted with EtOAc, the organic phase was separated and the aqueous phase was extracted three times with EtOAc. The combined organic phases were dried over Na$_2$SO$_4$ and the solvent was removed under vacuum to obtain 15 mg of crude.

The product was purified by flash column chromatography on silica gel (eluent: CH$_2$Cl$_2$/MeOH=98/2). Title compound was isolated as a clear oil. The product was fully characterized by NMR and Mass spectroscopy.

Starting from IXbisA a 50/50 mixture of 2 diastereoisomers was obtained in 43% yield.

Starting from IXbisB only 1 diastereoisomer was obtained in 53% yield.

Desired product: Compound (I) single diastereomer (trans-diastereomer) obtained from IXbisB; P=Ac Mass (ESI+) m/z=294 [M+Na]$^+$ $^1$H-NMR (300 MHz, CDCl$_3$):

δ 7.30 (m, 1H); 6.95 (m, 2H); 5.30 (bd, 1H); 4.46 (d, 1H); 4.38-4.31 (m, 1H); 4.07 (d, 2H); 3.70 (d, 1H); 2.39.2.33 (m, 2H); 1.81 (s, 3H).

It is thus evident to a person skilled in the art how the process according to the invention, besides having very high yields, makes it possible to simply and efficiently obtain a key synthon in the preparation of pharmaceutical active ingredients, in particular omarigliptin, bearing the correct steric configuration at all three of the chiral centers present in the molecular structure.

The invention claimed is:

1. A process for preparing a compound of formula (I):

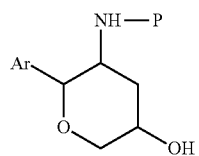

wherein Ar is phenyl optionally substituted with one to five R substituents, each R is independently selected from halogen, (C$_1$-C$_4$)-alkyl, optionally substituted by halogen, or (C$_1$-C$_4$)-alkoxy, optionally substituted by halogen;

and P is a primary amine protecting group;

the process comprising:

a) reacting, in the presence of a basic species or a catalyst, a compound of formula (II):

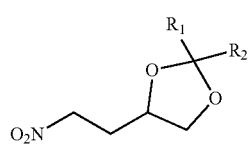

wherein each R$_1$ and R$_2$ is independently hydrogen or (C$_1$-C$_4$)-alkyl, or, wherein R$_1$ and R$_2$, when taken together, form a (C$_3$-C$_7$)-cycloalkyl group;

with a compound of formula (III):

Ar—CHO     (III)

wherein Ar is as defined above;

to give a compound of formula (IV):

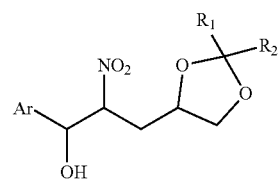

wherein Ar, R$_1$ and R$_2$ are as defined above; and b) converting a compound of formula (IV) into a compound of formula (I).

2. The process according to claim 1, wherein said basic species is selected from the group consisting of alkaline hydroxides, alkaline alkoxides, carbonates and tertiary amines.

3. The process according to claim 1, wherein said catalyst is an organometallic complex of Cu(II) or Cu(I) with a chiral ligand.

4. The process according to claim 3, wherein said chiral ligand is N-[(1S,2S,4S)-1,7,7-trimethylbicyclo[2.2.1]hept-2-yl]-2-Pyridinemethanamine (Ligand F) or 2,4-di-tert-butyl-6((E)-((R)-(6-methoxy-quinolin-4-yl)((2R,4S,8R)-8-vinyl-quinuclidin-2-yl)-methyl-imino)-methyl)-phenol (Ligand G).

5. The process according to claim 1, wherein step a is carried out in an organic solvent selected from the group consisting of methanol, ethanol, acetonitrile, diethoxyethane, 2,2-dimethoxypropane, 1,2-dimethoxyethane, dioxane, THF and toluene.

6. The process according to claim 1, wherein step a is carried out at a temperature ranging from −20° C. to 20° C.

7. The process according to claim 1, wherein each of R$_1$ and R$_2$ is a methyl group, or, wherein R$_1$ and R$_2$, when taken together, form a cyclohexyl group.

8. The process according to claim 1, wherein Ar is 2,5-difluorophenyl.

9. The process according to claim 1, further comprising:

c) chemoselectively reducing the compound of formula (IV) to give an amino-alcohol of formula (V):

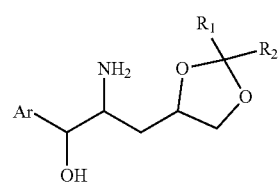

d) protecting the amino group to give a compound of formula (VI):

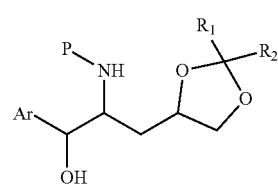

e) deprotecting the diol residue to give a compound of formula (VII):

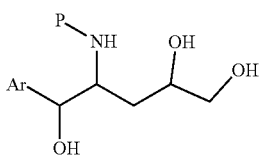
(VII)

f) regioselectively activating the primary hydroxy group to give a compound of formula (VIII):

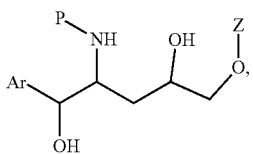
(VIII)

wherein Z is an organo sulfonyl group;

g) chemoselectively protecting a secondary hydroxy group to give a compound of formula (IX):

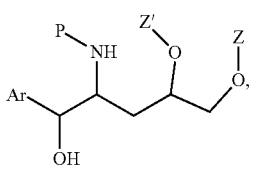
(IX)

wherein Z' is a hydroxy protecting group;

h) performing a base-catalyzed cyclization to give a compound of formula (X):

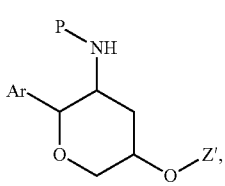
(X)

and i) deprotecting the secondary hydroxy group to give a compound of formula I.

10. The process according to claim 9, wherein Z is a tosyl group and Z' is a tetrahydropyranyl group.

11. The process according to claim 1, further comprising reacting a compound of formula (I) with an oxidizing agent in a presence of a solvent to convert the compound of formula (I) into a compound of formula Ibis (Ibis):

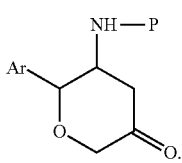
(Ibis)

12. The process according to claim 11, further comprising converting a compound of formula (Ibis) to omarigliptin.

13. The process according to claim 9, further comprising reacting a compound of formula (I) with an oxidizing agent in a presence of a solvent to convert the compound of formula (I) into a compound of formula (Ibis):

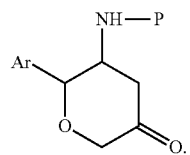
(Ibis)

14. A compound of formula (IV):

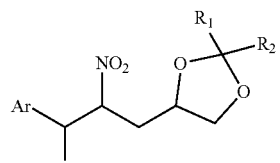
(IV)

wherein Ar is phenyl, optionally substituted with one to five substituents, each R is independently selected from halogen, $(C_1\text{-}C_4)$-alkyl, optionally substituted by halogen, or $(C_1\text{-}C_4)$-alkoxy, optionally substituted by halogen; and wherein each $R_1$ and $R_2$ is independently hydrogen or $(C_1\text{-}C_4)$-alkyl, or wherein $R_1$ and $R_2$, when taken together, form a $(C_3\text{-}C_7)$-cycloalkyl group.

15. A compound having a formula:
1-(2,5-difluorophenyl)-2-nitro-3((S)-1,4-dioxaspiro[4.5]decan-2-yl)propan-1-ol (IV)
or
1-(2,4,5-trifluorophenyl)-2-nitro-3-((S)-1,4-dioxaspiro[4.5]decan-2-yl)propan-1-ol (IV).

16. A process for preparing a compound of formula (IV):

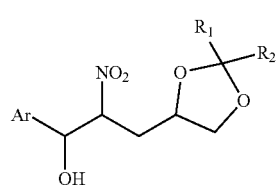
(IV)

wherein Ar is phenyl optionally substituted with one to five R substituents, each R is independently selected from halogen, $(C_1\text{-}C_4)$-alkyl, optionally substituted by halogen, or $(C_1\text{-}C_4)$-alkoxy, optionally substituted by halogen; wherein each $R_1$ and $R_2$ is independently hydrogen or $(C_1\text{-}C_4)$-alkyl, or, wherein $R_1$ and $R_2$, when taken together, form a $(C_3\text{-}C_7)$-cycloalkyl group; the process comprising:

a) reacting, in the presence of a basic species or a catalyst, a compound of formula (II):

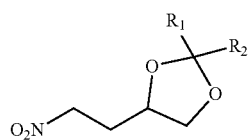
(II)
wherein $R_1$ and $R_2$ are as defined above;
with a compound of formula (III):
Ar—CHO (III)
wherein Ar is as defined above.
17. The process according to claim 16, wherein each of $R_1$ and $R_2$ is a methyl group or, wherein $R_1$ and $R_2$ when taken together, form a cyclohexyl group.
18. The process according to claim 16, wherein Ar is 2,5-difluorophenyl.
* * * * *